(12) United States Patent
Goldschmidt et al.

(10) Patent No.: US 8,891,088 B2
(45) Date of Patent: Nov. 18, 2014

(54) TOTAL INTERNAL REFLECTION PHOTOACOUSTIC SPECTROSCOPY

(71) Applicant: The Curators of the University of Missouri, Columbia, MO (US)

(72) Inventors: Benjamin Samuel Goldschmidt, Columbia, MO (US); Amanda Susan Martin Sudduth, Columbia, MO (US); Paul James Douglas Whiteside, Joplin, MO (US); John Andrew Viator, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 13/747,172

(22) Filed: Jan. 22, 2013

(65) Prior Publication Data

US 2013/0229660 A1 Sep. 5, 2013

Related U.S. Application Data

(60) Provisional application No. 61/632,247, filed on Jan. 20, 2012.

(51) Int. Cl.
| | | |
|---|---|---|
| *G01N 21/55* | (2014.01) | |
| *G01J 3/42* | (2006.01) | |
| *G01N 21/17* | (2006.01) | |

(52) U.S. Cl.
CPC ............... *G01J 3/42* (2013.01); *G01N 21/552* (2013.01); *G01N 21/1702* (2013.01)
USPC ............................................ 356/445; 356/73

(58) Field of Classification Search
USPC ................. 356/445, 73; 435/4, 287.1, 7.1, 29, 435/288.7; 436/63, 52, 164, 518, 534; 73/861.25, 861.26
See application file for complete search history.

(56) References Cited

U.S. PATENT DOCUMENTS

| | | |
|---|---|---|
| 2008/0014574 A1 | 1/2008 | Viator et al. |
| 2009/0170149 A1 | 7/2009 | Viator et al. |
| 2010/0285518 A1 | 11/2010 | Viator et al. |
| 2012/0064566 A1 | 3/2012 | O'Brien et al. |

OTHER PUBLICATIONS

Goldschmidt et al., "Total Internal Reflection Photoacoustic Spectroscopy for the Detection of beta-Hematin", Journal of Biomedical Optics, 2012; pp. 1-8, vol. 17, No. 6.
Viator, "Characterization of Photoacoustic Sources in Tissue Using Time Domain Measurements", Oregon Graduate Institute of Science & Technology, Portland, Oregon, Aug. 2000.
Muessing et al., "Total Internal Reflectance Optoacoustic Spectroscopy", Journal of Applied Physics, 1983, pp. 4251-4253, vol. 54, No. 8.
Viator et al., "Depth Profiling of Absorbing Soft Materials Using Photoacoustic Methods", IEEE Journal of Selected Topics in Quantum Electronics, 1999, pp. 989-996, vol. 5, No. 4.
Hinoue et al., "Photoacoustic Observation of Solid-Liquid Interface by Means of Total Internal Reflection Technique", Chemistry Letters, 1983, pp. 225-228.

*Primary Examiner* — Tri T Ton
(74) *Attorney, Agent, or Firm* — Thompson Coburn LLP

(57) ABSTRACT

A system and method of conducting total internal reflection photoacoustic spectroscopy (TIRPAS) comprising using a pulsed laser source to emit a thermally or stress confined laser beam at a prism comprising a surface to be in contact with a sample such that the laser beam travels through the prism to a location at an interface between the prism and the sample to form an evanescent field extending into the sample to generate a detectable photoacoustic response to the evanescent field by an analyte in the sample.

19 Claims, 13 Drawing Sheets

TOTAL INTERNAL REFLECTION PHOTOACOUSTIC SPECTROSCOPY

CROSS-REFERENCE TO RELATED APPLICATIONS

The present application is a non-provisional application claiming the benefit of the U.S. provisional patent application Ser. No. 61/632,247 filed Jan. 20, 2012, which is incorporated herein by reference in its entirety.

FIELD OF THE INVENTION

The present invention relates to photoacoustic spectroscopic analysis, more specifically, to total internal reflection photoacoustic spectroscopic analysis employing laser pulses of a short duration.

BACKGROUND OF INVENTION

Sensors using an evanescent field have become extremely useful in the past few years. These sensors have been created to detect a wide variety of materials such as pesticides, pathogens, nucleic acids, gases, and disease markers such as the HER2 breast cancer marker. These sensors function by measuring the interaction of an evanescent field (a non-propagating near field optical wave) with a target.

Total Internal Reflection Photoacoustic Spectroscopy (TIRPAS) is a method that exploits the evanescent field of a laser pulse reflecting off a glass/sample interface to generate photoacoustic responses. Specifically, the photoacoustic responses are typically generated by light absorbing analytes in a fluid sample (typically a liquid) that is in contact with a prism in the event one or more of the analytes are within the penetration depth of the evanescent field because upon absorbing the light energy the temperature of the analyte rapidly increases causing a rapid expansion (typically thermo-elastic) that in turns results in the formation of acoustic waves that propagate through the sample to a sensor.

For example, TIRPAS has been employed to detect dyes in a sample. Hinoue et al., *Photoacoustic Observation of Solid-liquid Interface by Means of Total Internal Reflection Technique*, CHEMISTRY LETTERS, 225-228 (1983). Hinoue et al. used a laser pulse generated with an optically chopped continuous beam HeNe laser at 632.8 nm to detect Brilliant Blue FCF dye at different angles of incidence to generate the evanescent field with a lock-in amplifier, which only amplifies a specific frequency, to detect the resulting acoustic wave. Although TIRPAS is typically used to analyze liquid samples, it may be used on gaseous and solid samples. See, e.g., Muessig et al., *Total Internal Reflectance Optoacoustic Spectroscopy*, J. APPL. PHYS. 54(8), 4251-4253 (1983). Muessig et al. also used continuous laser irradiation but instead of using an optical chopper to produce laser pulses, Muessig et al. used an oscillator connected to a lock-in amplifier to produce laser pulses.

Although TIRPAS has been known for more than thirty years its use has been limited due to shortcomings. For example, the TIRPAS disclosed by Hinoue et al. was limited to detecting Brilliant Blue FCF dye, a relatively high absorption analyte. Thus, it is unable to provide meaningful detection of low absorption analytes such as those that may be present in biological samples. In view of the foregoing, a need still exists for system(s) and method(s) for conducting TIRPAS that reduces or eliminates one or more of the foregoing shortcomings.

SUMMARY OF INVENTION

One embodiment of the present invention is directed to a system for conducting total internal reflection photoacoustic spectroscopy (TIRPAS). The system comprising: a pulsed laser source for emitting a thermally or stress confined laser beam; a prism comprising a surface to be in contact with a sample that is to be subjected to TIRPAS, wherein the laser beam and the prism, when conducting TIRPAS, are configured such that the laser beam travels through the prism to a location at an interface between the prism and the sample at an angle of incidence such that an evanescent field extending into the sample forms; and a detector for determining whether a photoacoustic response to the evanescent field is generated by an analyte in the sample.

Another embodiment of the present invention is directed to a method of conducting total internal reflection photoacoustic spectroscopy (TIRPAS). The method comprising: directing a thermally or stress confined laser beam at a prism comprising a surface in contact with a sample at an angle of incidence, wherein the laser beam and the prism are configured such that the laser beam travels through the prism to a location at an interface between the prism and the sample and forms an evanescent field extending into the sample; and determining whether a photoacoustic response to the evanescent field is generated by an analyte in the sample.

DETAILED DESCRIPTION OF INVENTION

Figure 1:
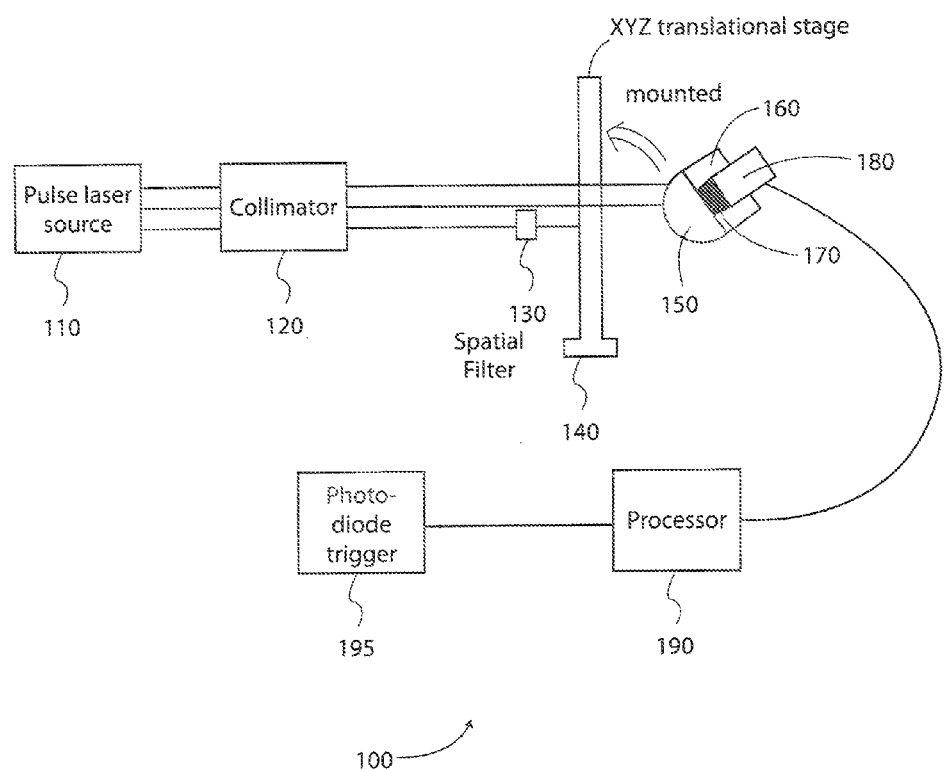
FIG. 1 is a schematic diagram of a system for detecting an analyte suspended in a fluid medium by TIRPAS according to an embodiment of the present invention.

One or more of the embodiments of the present invention reduce or eliminate one or more of the above-mentioned shortcomings with previous systems and/or methods for conducting TIRPAS by, among other things, providing, using, and/or performing one or more of the following: a relatively high peak power pulsed laser beam, changing or controlling the degree of collimation of the laser beam, changing or controlling the polarization of the laser beam, changing or controlling the cross-sectional diameter of the laser beam, and more precisely changing or controlling the angle of incidence of the laser beam (e.g., in smaller increments).

More specifically, one embodiment of the present invention is directed to a system for conducting TIRPAS that comprises (a) a pulsed laser source for emitting a thermally confined laser beam; (b) a prism comprising a surface to be in contact with a sample that is to be subjected to TIRPAS, wherein the pulsed laser source and the prism, when conducting TIRPAS, are configured such that the pulsed laser beam travels through the prism to an interface location between the prism and the sample and forms an evanescent field extending into the sample; and (c) a detector for determining whether a photoacoustic response to the evanescent field is generated by an analyte in the sample. In conducting TIRPAS, the thermally confined laser beam is directed at a prism and travels through the prism to the interface location and forms an evanescent field extending into the sample and it is determined whether a photoacoustic response to the evanescent field is generated by an analyte in the sample.

Pulsed Laser Source

It has been discovered that the limited ability of previously known TIRPAS systems/methods to detect lesser light absorbing analytes is due, at least in part, to the relatively low peak-power of the lasers that were used. For example, the detection limit in aforementioned Brilliant Blue FCF dye study conducted by Hinoue et al. was about $4.5 \times 10^{-3}$ absorbance units. Additionally, the low peak power laser beam requires the laser beam to be tightly focused on the prism surface, which results in a detection zone of relatively limited size. Further, it has been discovered that low peak laser power limits the type of information that can be obtained using TIRPAS.

As mentioned above, unlike previously known systems and methods for conducting TIRPAS, the system and method of the present for conducting TIRPAS utilizes a pulse laser source, which tend to be capable of producing a relatively high peak power (e.g., 1 Megawatt or more) as compared to a continuous wave laser source. It is believed the increased peak power of the pulsed laser beam contributes, at least in part, to a number of advantages when conducting TIRPAS. First, the use of a pulsed laser tends to reduce or eliminate the need for tightly focusing a laser beam and tends to allow for a larger detection zone. This larger detection zone, in turn, allows for the detection of difficult to detect analytes (e.g., myoglobin). Second, using a pulsed laser beam tends to result in more diverse frequency components of the acoustic waves, which is useful in the sense that a signal from one analyte is more likely to have one or more frequencies that will allow for it to be distinguished from one or more different analytes. Third, higher peak power tends to result in stronger or louder acoustic waves or signal being produced, which tends to enhance detection.

In one embodiment, the pulse laser source emits a thermally confined laser beam. It has been discovered that thermal confined laser pulses tend to result in louder acoustic responses than continuous wave lasers with optical choppers. In photoacoustics, the thermal confinement equation describes a condition where, if the pulse of the incident light occurs faster than the thermal confinement time, the resulting acoustic wave emitted is independent of heat conduction in the sample. This allows for thermal properties to be extracted from the data. For example, utilizing the thermal confinement condition $\tau \leq \delta/\alpha$, the acoustic pulse will be independent of heat conduction in the sample.

In another embodiment, the pulse laser source emits a stress confined laser beam, which tends to result in acoustic responses that are louder than those resulting from a thermally confined laser beam. As discussed in more detail below, a stress confined laser beam will also be thermally confined because thermal energy propagates slower than stress. It is presently believed that this louder acoustic response is due, in part, because stress confined lasers typically can produce larger peak power beams than thermally confined lasers. Additionally, it is presently believed that using a stress confined pulsed laser to conduct TIRPAS rather than a thermally confined pulsed laser has the potential to allow users to obtain and/or improve the accuracy in determining the following: information about the propagation of the evanescent field through a material in the similar manner as to that disclosed by Viator et al., *Depth Profiling of Absorbing Soft Materials Using Photoacoustic Methods*, IEEE J. SEL. TOP. QUANT. ELECTRON. 5(4), 989-996 (1999); information about optical properties such as refractive index; acoustic representations of evanescent fields; and depth profiling of nanostructures (due to a stress confined pulse being short enough that the acoustic response mirrors how the evanescent field interacted with the absorbers on the nanoscale). Although stress confined lasers offer advantages over thermally confined lasers such as described above, stress confined lasers in the picosecond range tend to be quite expensive in comparison to thermally confined lasers. So, thermally confined lasers are likely to be selected after conducting a cost-to-benefit analysis for each type of laser.

To be clear, thermal and stress confinement depend upon the material or absorber that is being subjected to the laser and is not truly a characteristic of the laser. That said, a person or ordinary skill in the art often refers to lasers as being thermally- or stress-confined. The thermal confinement and stress confinement thresholds are represented by the following equations:

$$\tau_{th} = \delta^2/\alpha$$

$$\tau_{stress} = \delta/\sigma$$

where $\delta$ is the thickness of the absorber or the optical penetration depth of the absorber in photoacoustic spectroscopy and the actual penetration depth of the evanescent field or the thickness of the absorber if it is smaller than the penetration depth, $\alpha$ is the thermal diffusivity of the absorber, and $\sigma$ is the speed of sound in the absorber. For most, if not all, biological samples may be approximated using the thermal diffusivity of water, which is $0.143 \times 10^{-6}$ m$^2$/s, and the typical penetration depth will be on the order of the wavelength. So, when using for example a Q-switched Nd:YAG laser having a wavelength of 532 nm, the thermal confinement ($\tau_{th}$) threshold is about 1.98 microseconds and the stress confinement $\tau_{stress}$ threshold is about 0.355 nanoseconds. Thus, the laser pulse duration of 5 nanoseconds used in the Examples is shorter than the thermal confinement threshold so the laser beam is thermally confined but longer than stress confinement threshold so it is not stress confined. For gold, which has a thermal diffusivity of $1.27 \times 10^{-4}$ m$^2$/s, the thermal confinement threshold would be about 2.23 nanoseconds and the pulse duration of the aforementioned laser beam is close but greater than the threshold so it would not be thermally confined. The speed of sound in metals such as gold is about 10,000 m/s so the stress confinement threshold is about 53.2 picoseconds. For oil, which has a thermal diffusivity of $7.38\times10^{-8}$ m$^2$/s the thermal confinement threshold would be about 3.84 microseconds and the aforementioned pulse duration is shorter than the threshold so it would be thermally confined. For silicones, the speed of sound is about 100 m/s so the stress confinement threshold is about 5.32 nanoseconds and the aforementioned laser would be stress confined. Additionally, it should be noted that thermal confinement/stress confinement may be adjusted by adjusting the $\delta$ parameter (in this case, the evanescent field penetration depth) by adjusting the refractive index of the prism/sample interface, wavelength, and angle of incidence.

In one embodiment, the pulse laser source is a Q-switched laser. In another embodiment the pulse laser source is a Q-switched Nd:YAG laser. Other types of pulsed lasers, such as Gain-switched or Mode-locked, may be used. Compared to Mode-locking, Q-switching tends to lead to lower pulse repetition rates, higher pulse energies, and longer pulse durations. In short, a wide variety of lasers may be used in the system/method of the present invention. The selected laser is simply selected depending upon the intended use. For example, a laser may be selected provided it is capable of providing a pulse of light in a shorter duration than the thermal or stress confinement times, is of an appropriate wavelength, repetition rate, and energy and peak power levels depending upon the particular use. Specifically, the laser pulse should be of a wavelength that an analyte of interest can absorb. For most materials, this falls in the visible regime but infrared and UV wavelengths are often appropriate as well. Also, higher repetition rates tend to result in a better signal to noise ratio. Additionally, it should be noted that multiple laser beams or pulse laser sources may be employed to, for example, provide a larger detection area or they may be of different wavelengths to allow for the detection of different analytes.

Prism

As with the choice of laser, the choice of prism is not limited to a specific geometric shape. Rather, the shape and material are preferably selected for the particular application and may have an effect on whether other components are included in the system/method of the present invention. More precisely the geometric shape tends to affect the optical setup needed to obtain a collimated beam profile at the prism/sample interface. For example, if a hemicylindrical lens is used, a correcting cylindrical lens will be needed to keep the beam collimated at the interface. If a right angle prism is used, however, such optics are unlikely to be needed to correct the collimation. It should be noted that when orienting the prism that each degree of prism rotation does not equal a degree of change at the prism/sample interface because the optical refraction has to be taken into account.

In addition to prism shape, prism material is selected for the particular application in view of the wavelengths of light that are to be used to test the sample(s). For example, a glass prism is often a good choice when working with visible wavelengths, whereas a silicon prism is often a good choice when working with long infrared wavelengths.

Evanescent Field Penetration Depth

An evanescent field decays exponentially with distance from the interface into the sample and is most intense within two thirds of the penetration depth from the surface of formation. Typically, an evanescent field extends approximately one wavelength from the prism/sample interface. It is this very feature that makes TIRPAS a valuable tool, which may be used to accomplish or perform a variety tasks such as detecting the presence and/or concentration of harmful chemicals or agents in biological fluids with the disturbance of cellular components. More specifically, because many analytes of interest are of sizes that fall within the range of an order of magnitude larger of the penetration depth to an order of magnitude smaller than the penetration depth, they may be detected, differentiated, and/or separated by controlling the penetration depth of the evanescent field. As is disclosed in more detail below, the system/method of the present invention for conducting TIRPAS allows for previously unknown control over the penetration depth, which in turns contributes to previously unknown control over TIRPAS sensitivity.

In addition to detecting, differentiating, and/or separating based on size, an embodiment of the system/method of the present invention may be used to determine an absorption spectrum of an analyte based upon how loud the acoustic signal is for laser light at different wavelengths. This may be accomplished by measuring the peak-to-peak signal voltage and taking into account the differences in penetration depth ($d_p$), which depends upon four factors: wavelength of the incident light ($\lambda_0$), refractive index of the prism ($n_1$), refractive index of the sample ($n_2$), and the angle of incidence ($\theta_1$) in accordance with the following formula:

$$d_p = \lambda_0 / (2\pi \cdot n_1 \sqrt{\sin^2\theta_1 - (n_2/n_1)^2})$$

As the difference between the indexes of refraction approach each other (for total internal reflection to occur, however, the refractive index of the sample must be lesser than that of the prism), the penetration depth tends to increase (other things being equal).

Angle of Incidence

As mentioned above, the angle of incidence is one of the factors upon which the penetration depth depends. Specifically, total internal reflection occurs upon the angle of incidence equaling or exceeding the critical angle ($\theta_c$), which depends primarily on the optical properties of the prism and the sample.

Figure 4A:
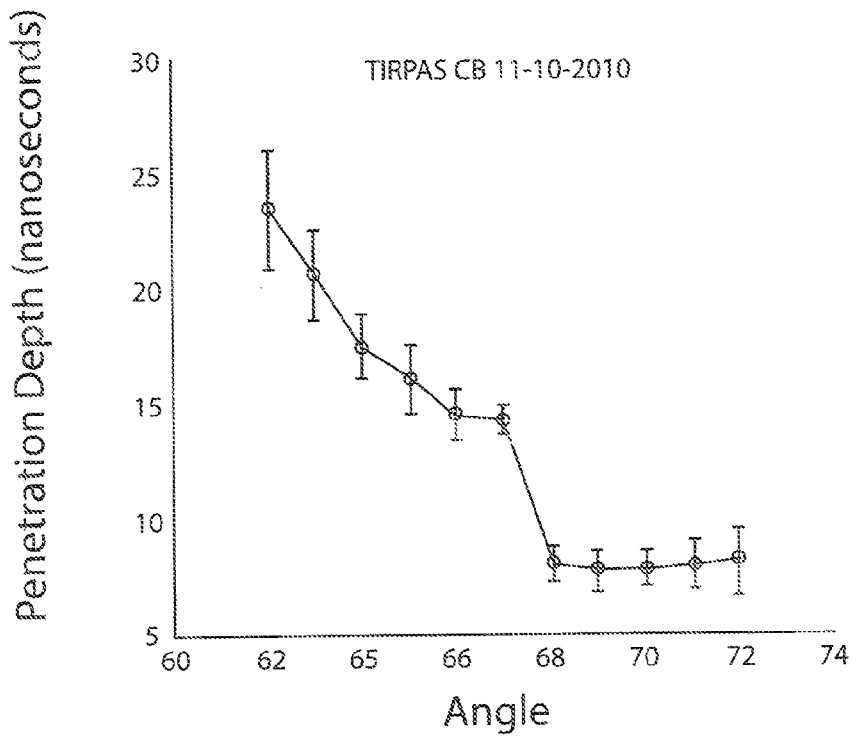
FIGS. 4A and B are graphs showing penetration depth as a function of incidence angle and the transition from photo acoustic spectroscopy (PAS) to TIRPAS.
Figure 4B:
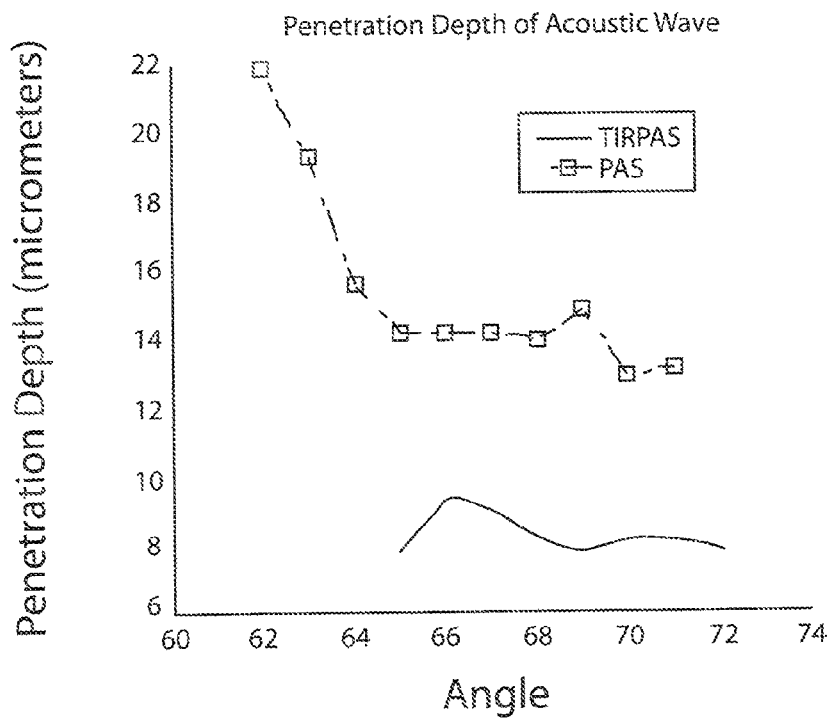

FIGS. 4A and 4B illustrate the differences between the penetration depths of PAS and TIRPAS excitations. Specifically, the penetration depth at non-totally internally reflected angles levels off as the angle is brought closer to the critical angle. When the angle of incidence equals the critical angle, the penetration depth decreases from that typical for PAS to that of an evanescent field. For the system used to generate FIG. 4, the sudden decrease in the penetration depth at an incidence angle that is between 66° and 68° in FIG. 4A corresponds to the critical angle ($\theta_c$). Regarding FIG. 4A, the penetration depth in nanoseconds in that the graph represents the duration the wave takes to go from its peak voltage to 1/e (which is about 37% of its peak voltage). To convert from time to distance, 1.5 micrometers is equivalent to 1 nanosecond.

Figure 5:
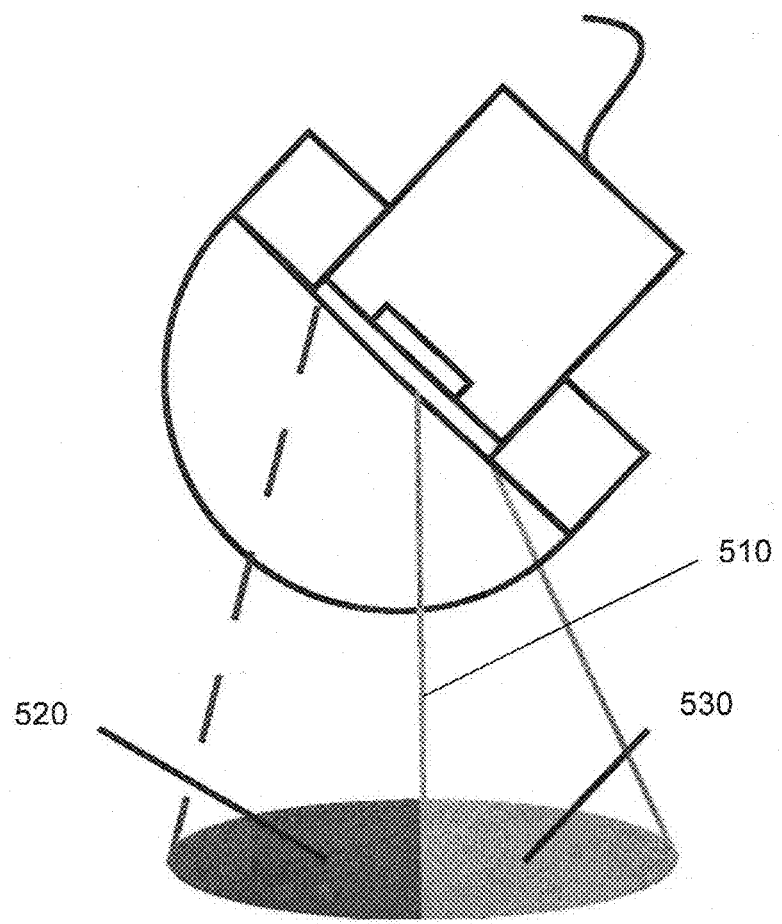
FIG. 5 is a schematic diagram showing divergent light after reflecting off a prism/fluid interface.
Figure 6:
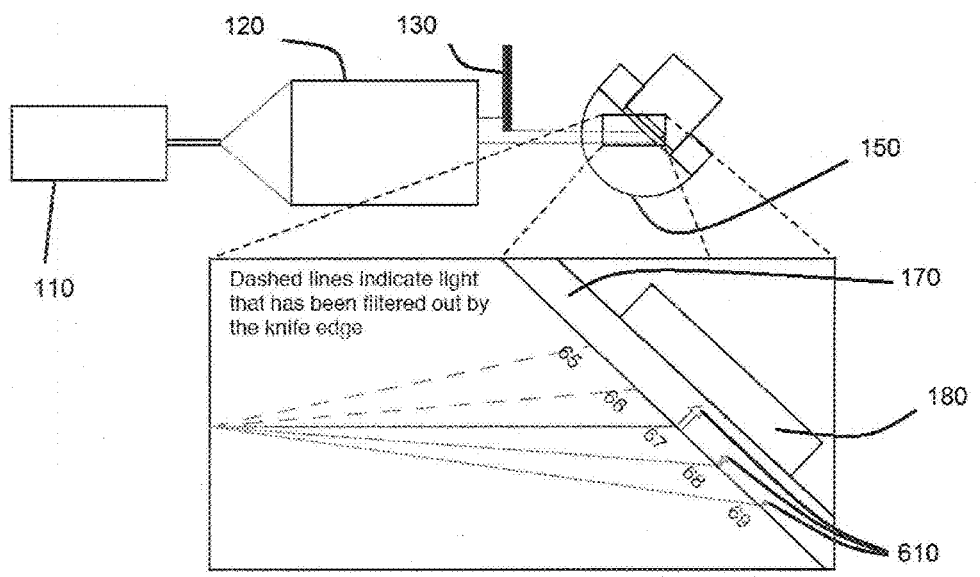
FIG. 6 is a schematic diagram of a system for detecting an analyte suspended in a fluid medium by TIRPAS according to an embodiment of the present invention.

For a non-zero divergent beam, the critical angle may be visually observed (using 1.5+OD safety goggles) in a reflected spot of a laser beam, a portion of which is undergoing total internal reflection, on a scattering surface located at the point the light exits the prism as depicted in FIG. 5. The reflected spot has two visibly different portions. A darker portion 520 due to the increased loss from the reflected light not under total internal reflection due to the continuum of divergence angles (i.e., the part of the beam in that may be used to conduct PAS) and lighter portion 530 that is indicative of the light that is undergoing evanescent absorption at the prism/sample interface (i.e., the part of the beam that may be used to conduct TIRPAS). The boundary line 510 indicates the position of where the critical angle occurs. Changing the angle of the prism relative to the incident laser beam shifts the position of the boundary line and thus the proportion of the spot that is undergoing total internal reflection. Embodiments of the method/system of the present invention allow for enhanced precision in changing or controlling the angle of incidence of the laser beam by, for example, using a spatial filter (which may allow for conducting TIRPAS and PAS independent of each other as depicted in FIG. 6), collimator, beam splitter, and/or an XYZ translational stage. For example, using an autocollimator in conjunction with a motor has resulted in the ability to adjust the increment by which the incidence angle may be changed to 0.01° or smaller. This enhanced control over the incidence angle tends to allow for more accurate control over the penetration depth of the evanescent field as described in herein.

Evaluating Analyte Association

Figure 8:
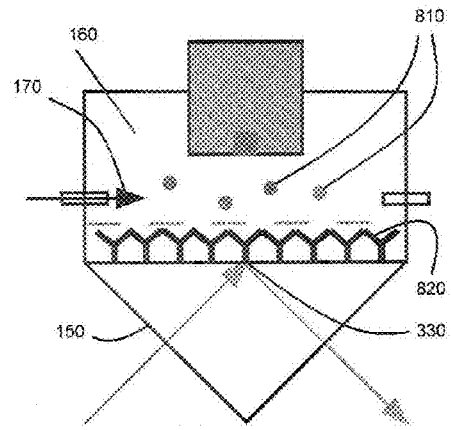
FIG. 8A-E is a schematic illustration of the steps for determining the speed at which materials bind to surfaces in real time according to an embodiment of the present invention.
Figure 8:
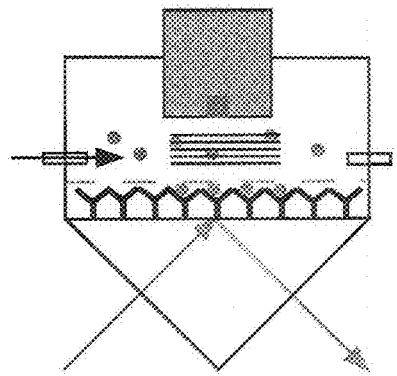
Figure 8:
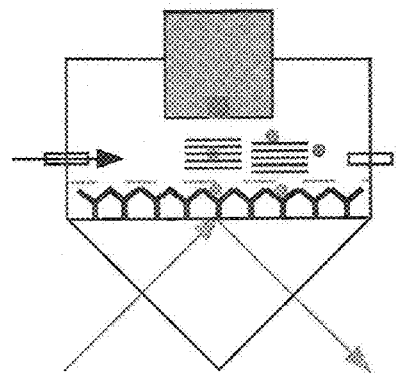
Figure 8:
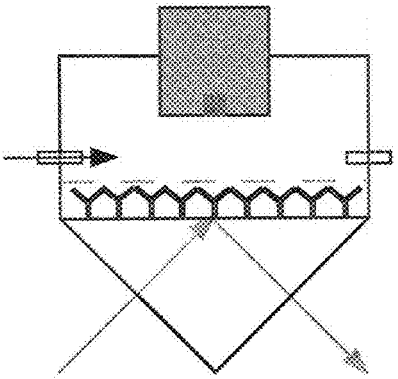
Figure 8E:
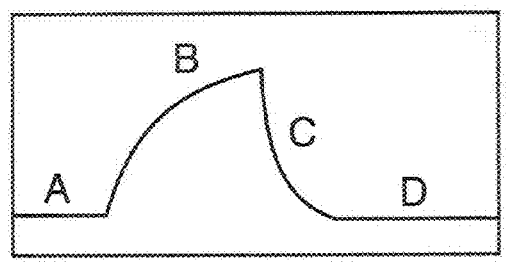

In addition to tending to enhance the sensitivity and accuracy of detecting light-absorbing analytes (e.g., biological compounds such as hemozoin in a blood sample, chemical compounds), one or more embodiments of the system and method for conducting TIRPAS of the present invention may be used to determine the rate at which an analyte that responds to an evanescent field associates with one or more materials, articles, compounds, surfaces, etc. located within the penetration depth of an evanescent field in real time. Referring to FIG. 8A-D, a fluid sample comprising a number of analytes 810 in the sample are being flowed (A) through the sample cavity 160, wherein said analytes 810 have a propensity to associate with articles 820 (e.g., antibodies) that are at or near the interface 330 between the prism 150 and the fluid sample 170. In particular, the penetration depth of the evanescent field may be adjusted to extend to about the outer surface of the articles 820 to more precisely determine the moment at which contact or adherence occurs. As analytes come within the penetration depth (B), acoustic responses to the evanescent field are generated by the analytes until such times as the analytes disassociate and are washed away (C) until returning to a baseline state (D). Thus, the data (e.g., peak-to-peak voltage) may be used to characterize the propensity to associate and/or dissociate qualitatively and/or quantitatively as shown in FIG. 8E.

Having disclosed an overview of embodiments of the present invention, exemplary figures depicting embodiments of the present invention are described below in order to provide a general context for various aspects of the present invention.

Embodiments Utilizing Collimator and Spatial Filter

Figure 3:
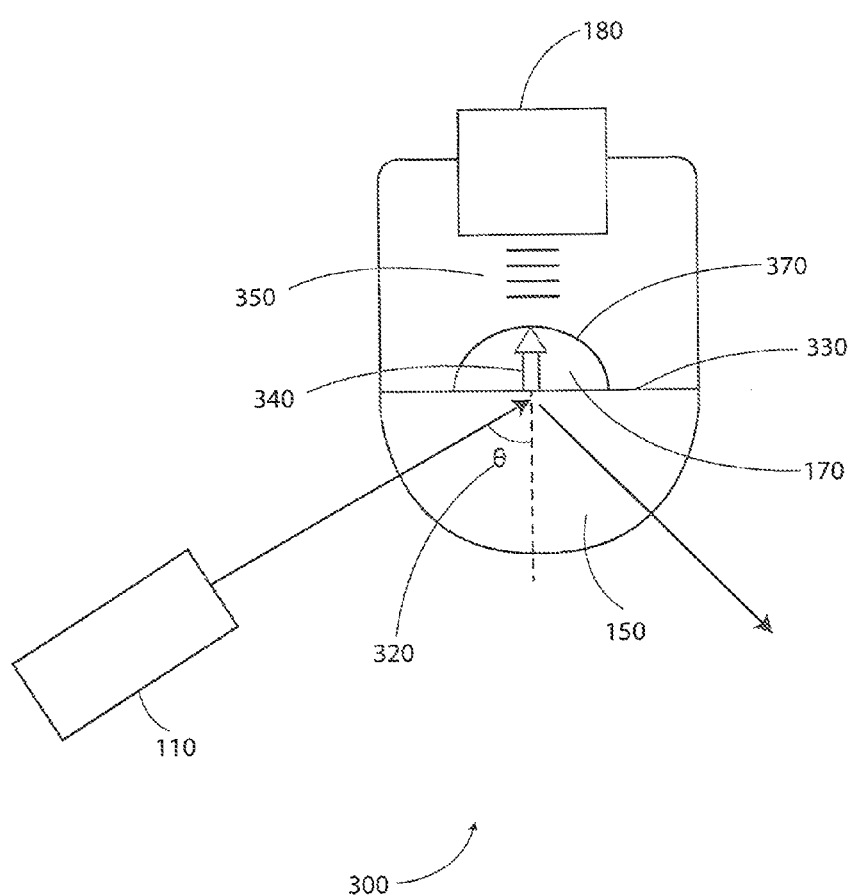
FIG. 3 is a schematic diagram illustrating TIRPAS of the system depicted in FIG. 1 in more detail.

Referring to FIGS. 1 and 3, schematic diagrams of a system 100 for detecting an analyte suspended in a fluid medium by TIRPAS according to an embodiment of the present invention. The system 100 includes a pulse laser source 110, a collimator 120, a spatial filter 130, an XYZ translational stage 140, a prism 150, a sample cavity 160 (fluid medium), a sample 170, a detector 180, a processor 190, and a photodiode trigger 195.

In the system 100, the laser beam from pulse laser source 110 (typically transmitted via fiber optic cable, not shown) is preferably configured to be aligned with the collimator 120 and the prism 150. The collimator 120 is placed between the pulse laser source 110 and the prism 150. The spatial filter 130 is mounted on the XYZ translational stage 140. The prism 150 and the sample cavity 160 are also preferably mounted on the XYZ translational stage 140. It is understood that essentially any prism with higher refractive index than that of the sample may be employed. In one embodiment, the depth of the sample cavity 160 is in the range of about 1 mm to about 10 mm. In one embodiment, the prism 150 is a 16 mm diameter hemicylindrical prism made from cut pieces of Simax semi-circular rod stock. Although sample cavity is depicted as a portion of the prism structure (i.e., a single unit comprising the prism and the cavity), this need not be the case and cavity may be formed as part of a separate structure.

The detector 180 is in contact with the sample 170 (typically a fluid) contained in the sample cavity 160, the sample may comprise one or more analytes (not shown). The detector 180 is in electronic communication with the processor 190. The processor 190 is in electronic communication with the photo-diode trigger 195, which is used to trigger the processor 190 and to sense when the pulse laser source 110 emits a laser beam. It should be noted that electronic communication may be accomplished through wires or a wireless network. For example, in one embodiment, the detector 180 is in electronic communication with the processor 190 through a wireless network. In this embodiment, the detector 180 transfers the information of the detected photoacoustic wave signals to the processor 190 through the wireless network. It is to be noted that if a wireless network is utilized it should be done in a manner such that it does not interfere with the acoustic signal.

In operation, the pulse laser source 110 emits a thermally confined laser beam. Preferably, the pulse laser source 110 emits a thermally confined laser beam at a pre-selected wavelength. The emitted laser beam is collimated by the collimator to ensure that the laser beam's incident photons are substantially parallel to each other as they reach the prism 150.

Some portion of the collimated laser beam may be filtered by the spatial filter 130 as shown in FIG. 6 to adjust or control the portion, if any of the laser beam that has an angle of incidence above and/or below the critical angle. For example, the spatial filter 130 may be used to ensure that the entirety of the laser beam has an incidence angle that is above the critical angle to ensure that the photoacoustic events are excited solely by the evanescent field as shown in FIG. 6 (the dashed lines indicate light that has been filtered by the spatial filter 130). The arrows 610 in FIG. 6 represents the extent of the evanescent field into the sample analyte. Any conventional spatial filter may be employed. In one embodiment, the spatial filter is a knife edge. By adjusting the spatial filter 130, TIRPAS and PAS measurements may be alternately conducted on a sample without having interfering signals.

The unfiltered portion of the beam continues to and through the prism 150, and preferably, is directed to a location at or near the interface between the prism 150 and the sample 170 (i.e., an interface location). If the pre-selected angle 320 is greater than or equal to a critical angle there will be total internal reflection and evanescent field 370 excitation will occur at the prism/fluid interface 330. If, however, the preselected angle 320 is smaller than a critical angle, evanescent field excitation will not occur and the laser beam rather than the evanescent field will penetrate the sample (i.e., photoacoustic spectroscopy). The pre-selected angle 320 can be adjusted by manipulating the XYZ translational stage 140 as explained in more detail below. In one embodiment, the prism 150 is mounted on the rotational XYZ translation stage 140 of FIG. 1. By rotating the XYZ translational stage 140, the angle of incidence can be adjusted. The XYZ translational stage 140 allows the system 100 to have more accurate control of the pre-selected angle 320, which in turn, provides significant improvement on the adjustment of the penetration depth of evanescent field. As an alternative to or in addition to the adjustable stage to which the prism is mounted, the fiber optic cable in communication with the pulse laser source 110, or if no fiber optic cable is used the pulse laser source itself may be mounted to an adjustable stage such as an XYZ translational stage. Thus the angle of incidence (i.e., the pre-selected angle 320) may be adjusted not only by adjusting the prism 150 but also through the control of the direction of the laser beam emitted by the pulse laser source 110. It should be noted that one or more stages adjustable in less than three dimensions may be used.

Thus a laser beam reaching the interface location at an angle at least equal to the critical angle excites or causes the formation of an evanescent field 370 that extends into the sample 170 a penetration depth 340. If one or more analytes (not shown) in the sample 170 are capable of absorbing the evanescent field energy are present within the penetration depth 340 of the evanescent field, the analytes undergo thermoelastic expansion and generate a photoacoustic wave 350 (i.e., a photoacoustic response) that travels to the detector 180 where it is detected.

The pulse laser source 110 may employ any thermal confined pulsed signal or multiple wavelength lasers as the excitation source. The wavelength is selected according to the analyte to be detected. In one embodiment, the pulse laser source 110 is a Q-switched Nd: YAG laser (Surelite I-20 doubled to 532 nm, Continuum, Santa, Calif.) coupled through 1000 µm 0.37 NA optical fiber (BFH37-1000, Thorlabs, Newton, N.J.). In one embodiment of the present invention, the pulse laser source 110 is pulsed at 20 Hz at a duration of 5 ns with energies ranging from 5 to 6 mJ.

The collimator 120 is employed to collimate the pulsed laser beam. Any conventional collimation lenses may be used for making the laser beam's incident photons more parallel to each other as they approach the prism. In one embodiment, the collimator 120 is a set of three optical lenses: the first lens is a Thorlabs NBK7 LA1509 plano-convex lens with a focal length of 100.0 mm; the second lens is a Thorlabs NBK7 LA 1131 plano-convex lens with a focal length of 50.0 mm; and the third lens is a Thorlabs SF11 LC2679 plano-concave lens with a focal length of 30.00 mm.

The detector 180 is in contact with the sample and is able to detect the photoacoustic response or wave generated by the analyte. In one embodiment, the detector 180 is a PVDF transducer. Preferably, the detector is amplified and more preferably the amplifier is a broadband amplifier. An example of an appropriate broadband amplifier is a model SF445A 350 MHz preamplifier made by Stanford Research Systems. An example of an appropriate processor 190 is a TDS 2024B 200 MHz four-channel digital storage oscilloscope available from Tektronix of Beaverton, Oreg. Preferably, the detector 180 and the processor 190 are connected through 50 ohm coaxial cable such as 2249-C-24 available from Pomona of Everett, Wash. An example of a photo-diode trigger 195 is a Thorlabs DET10A SI based photodiode trigger.

As mentioned above, the system of the present invention allows for the use of a laser beam with higher peak power, a higher energy photoacoustic response tends to be generated by analytes that absorb the evanescent field energy. Advantageously, the resulting higher energy acoustic waves tend to generate many frequencies of signal which may be interpreted to provide information about said analyte. Because of the high frequency electrical reflections, however, it is often desirable to match the impedance of the cabling and the amplifier to reduce or eliminate ringing that can occur without proper impedance matching even with the lower frequencies.

Figure 7:
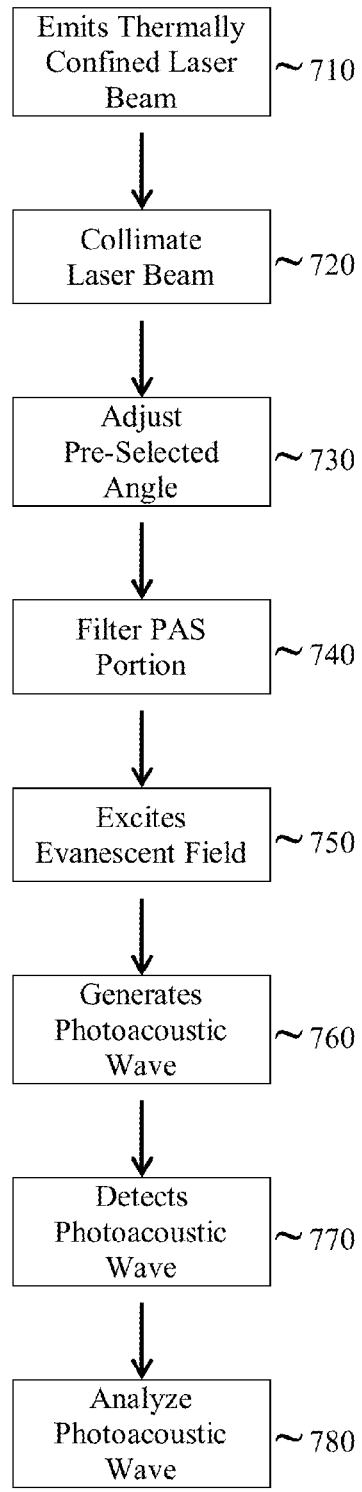
FIG. 7 is a flowchart of a method for detecting an analyte suspended in a fluid medium by TIRPAS according to an embodiment of the present invention.

Referring to FIG. 7, a flowchart of a method for detecting an analyte suspended in a fluid medium using the TIRPAS, at step 710, the pulse laser source 110 of FIG. 1 emits a thermally confined laser beam. Preferably, the laser beam is emitted at a pre-selected wavelength. The pre-selected wavelength is likely determined based on an absorption coefficient that is specific to an analyte in the sample. Next, at step 720, the laser beam is subjected to the collimator to ensure that the laser beam's incident photons are substantially parallel to each other as they reach the prism 150. It is to be noted that, collimating is most likely unnecessary if the laser beam is coming directly out of the laser cavity but collimation is utilized if the laser beam is focused into an optical fiber (which loses the collimation) and then is recollimated after exiting the fiber. Next, at step 730, the XYZ transitional stage 140 may be adjusted to ensure that the laser beam enters the prism 150 at a pre-selected angle. Next, at step 740, the spatial filter 130 may be adjusted to ensure that only TIRPAS excitation undergoes on the spot of the prism/fluid interface 330 where the laser beam hits. Alternatively, the spatial filter 130 may also be adjusted to block the TIRPAS spot for the purposes of testing PAS detection. Alternatively, both the XYZ transitional stage 140 and the spatial filter 130 can be used together to help maximize the evanescent field 370 excitation at the prism/sample interface 330 at step 750. Upon the excitation, the evanescent field 370 extends into the sample and is absorbed by an analyte in the sample 170 at step 760. In response, the analyte thermoelastically expands and generates the acoustic wave 350. Next, at step 770, the detector detects the acoustic wave 350. At step 780, the acoustic wave 350 is analyzed to determine certain characteristics of the analyte. In one embodiment, a software program may be used to determine the penetration depth of the evanescent field as described in greater detail below.

In one embodiment, a software program is employed to analyze the photoacoustic wave signals to determine the penetration depth of the photoacoustic waveforms obtained by the detector 180. In this embodiment, the software program can be installed and operated in any suitable computer readable medium. In addition, by using the software program, the detector 180 can automatically detect the photoacoustic wave signals generated by the analyte and store such information in its storage element. A copy of the source code is appended hereto. In this embodiment, a graphical user interface (GUI) (e.g., an oscilloscope) is provided so that the user may be informed with a visualized interface of the result of the detection of the analyte. The use of the software program may increase the speed with which a system/method of the present invention analyzes a single waveform.

Figure 9:
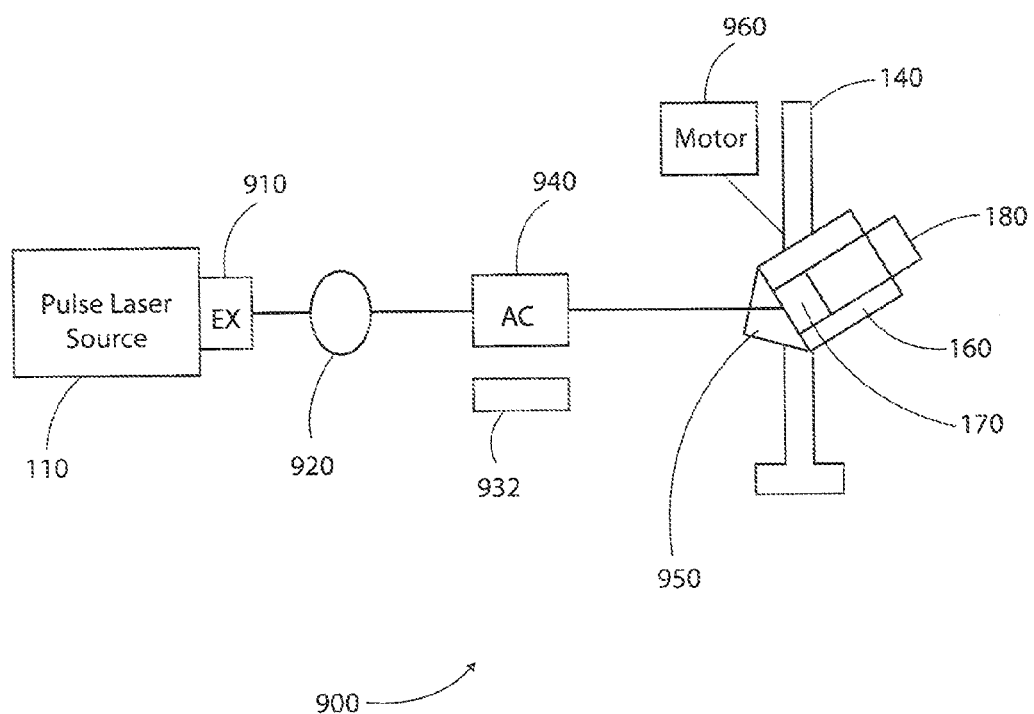
FIG. 9 is a schematic drawing of a system for detecting an analyte suspended in a fluid medium by TIRPAS according to an embodiment of the present invention.

Embodiment Comprising Beam Expander, Aperture, Beam Splitter, and Autocollimator Referring to FIG. 9, embodiment 900 includes a pulse laser source 110, a sample cavity 160, a sample 170, a detector 180, a beam expander 910, a variable aperture 920, a fluorescent card 932, an autocollimator 940, a prism 950 (in this case a right-angle prism), and a motor 960. In operation, the system 900 embodiment functions much like the system 100 embodiment but the system 900 embodiment allows for more precise control of the angle of incidence and the collimation of the laser beam. For example, the laser beam may be directed through a beam expander 910 and a variable aperture 920, which may be used to adjust the size (cross-section or spot size) of the laser beam to, preferably, reduce or eliminate acoustic diffraction of the laser beam. This is particularly useful in the event one is interested in analyzing acoustic wave qualities other than just the peak-to-peak signal The autocollimator 940 and fluorescent card 932 are used prior to, not while, conducting TIRPAS to enhance the alignment of the laser beam. Specifically, the autocollimator 940 is manipulated to make two beams reflecting on the fluorescent card 932 overlap to help ensure that the laser beam is aligned to be perpendicular to the surface of prism 950 as it enters the prism. The laser beam collimated by the autocollimator 940 is directed to hit the right-angle prism 950, which was selected to help keep the collimation more constant. Additionally, it is desirable to confirm that the prism and the autocollimator are properly aligned. This may done, for example, by using a digital level to level the prism with respect to a table. Specifically, the autocollimator levels the laser beam relative to an optical table and the digital level is used to level the prism relative to the optical table.

Motor 960, preferably a stepper motor, is for adjusting the orientation of prism 950 to control the angle of incidence. Preferably, the motor 960 is run by a PXI card. The PXI card allows the motor 960 to programmatically control the laser beam so that tuning of the incidence angle of the laser beam can be performed in small increments such as 0.01° or less. In fact, increment adjustments as small as 0.0025° have been achieved.

Figure 2:
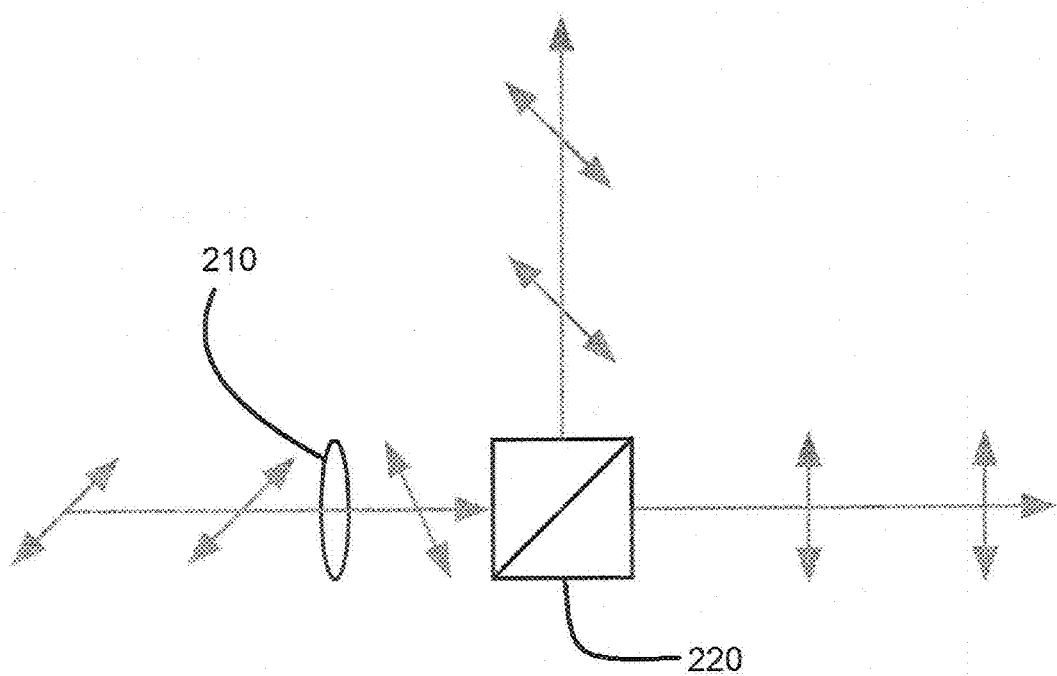
FIG. 2 schematic diagram illustrating a polarization feature that may be incorporated in embodiments of the present invention.

In the event polarization of the laser beam is lost, for example, during transmission in an optical fiber or after reflection by several mirrors, the beam may be re-polarized. One manner of re-polarizing or controlling the polarization of the beam is shown in FIG. 2 in which a waveplate 210 rotates the polarization of the laser beam and it then is directed through a polarizing beam splitting cube 220, which selectively transfers more or less total energy out of each side of the cube depending upon the light's incident polarization. The waveplate 210 and polarizing beam splitting cube 220 may be used independently or together depending upon the desired effect. For example, if one wants to simply rotate the polarization, the waveplate 210 would be used to, for example, rotate vertically polarized light coming from a laser cavity into horizontally polarized light (or any angle in between, without the polarizing beam splitting cube 220.

Advantageously, either of the polarizations may be used to excite analytes in samples under the TIRPAS. Additionally, this may be employed in controlling the effective thickness of the evanescent field, wherein the effective thickness is equivalent to path length (L) in Beer's law, $A=\epsilon cL$, wherein $\epsilon$ represents molar absorbtivity and c represent the concentration of a compound. The actual penetration depth of the evanescent field does not change, but due to changes in the electric field between the two polarizations the "net" absorption of a material will be different between them due to this difference in electric field from the difference in polarization. For thin materials (materials smaller than the penetration depth), the effective thickness of the evanescent field may be determined according to the following equations:

$$d_{e.i.} = \frac{4n_{21}d\cos\theta}{(1-n_{31}^2)}$$

$$d_{e\parallel} = \frac{4n_{21}d\cos\theta[(1+n_{32}^4)\sin^2\theta - n_{31}^2]}{(1-n_{31}^2)[(1+n_{31}^2)\sin^2\theta - n_{31}^2]}$$

where $n_{21}$ is $n_2/n_1$ where $n_2$ is the refractive index of the thin film sample and $n_1$ is the refractive index of the prism, $n_{32}$ is $n_3/n_2$ where $n_3$ is the refractive index of the material beyond the thin film sample (e.g., air, water, or whatever material or medium the film is in), $n_{31}$ is $n_3/n_1$, $\theta$ is the angle of incidence. For bulk materials (materials larger than the penetration depth evanescent field), the effective thickness of the evanescent field may be determined according to the following equations:

$$\frac{d_{e\perp}}{\lambda_1} = \frac{n_{21}\cos\theta}{\pi(1-n_{21}^2)(\sin^2\theta - n_{21}^2)^{\frac{1}{2}}}$$

-continued $$\frac{d_{e\parallel}}{\lambda_1} = \frac{n_{21}\cos\theta(2\sin^2\theta - n_{21}^2)}{\pi(1-n_{21}^2)(\sin^2\theta - n_{21}^2)^{\frac{1}{2}}[(1+n_{21}^2)\sin^2\theta - n_{21}^2]}$$

where $n_{21}$ is $n_2/n_1$, $\theta$ is the angle of incidence, and $\lambda_1$ wavelength of the incident light.

EXAMPLES

System

The system depicted in FIG. 1 was used in the examples. The laser was a Q-switched Nd:YAG laser (Surelite I-20 doubled to 532 nm, Continuum, Santa Clara, Calif.) was coupled through 1000 μm 0.37 NA optical fiber (BFH37-1000, Thorlabs, Newton, N.J.). The laser was pulsed at 20 Hz at a duration of 5 nanoseconds with energies ranging from about 5 to about 6 mJ. The optical fiber was coupled to a set of lenses—in the order of 100 mm (LA1509, Thorlabs), 50 mm (LA1131) and −30 (LC2679)—to collimate the output before entering the hemicylindrical prism, which was mounted to an XYZ stage (481-A, Newport, Irvine, Calif.). The stage allowed the prism to be adjusted to position the total internal reflected spot as well as to change the angle of incidence of the incoming laser light.

A gold coated PVDF transducer was used as the detector. Specifically, the transducer is similar to the designs disclosed in J. A. Viator, *Characterization of Photoacoustic Sources in Tissue Using Time Domain Measurements*, OREGON GRADUATE INSTITUTE OF SCIENCE & TECHNOLOGY, Portland, Oreg. (August 2000), except that the element was not etched and a layer of silicone was added to protect the sensing material and to prevent the sample from staining the transducer. This coating did not introduce significant reflections due to its close impedance match with the sample, which was mostly water. The acoustic impedance of the silicone was 1.1 MRayls whereas the impedance of water is 1.5 MRayls. At normal incidence this difference gives a reflection coefficient of approximately 2%. In addition, a brass mask was used to create a 0.5 cm×0.5 cm square active area in the center of the transducer to be used as the detection area.

The voltage response of the transducer was amplified by a 350 Mhz preamplifier (SR445A, Stanford Research Systems, Sunnyvale, Calif.). The amplifier was then attached to a 200 Mhz four-channel digital storage oscilloscope (TDS 2024B, Tektronix, Beaverton, Oreg.) through 500 coaxial cable (2249-C-24, Pomona, Everett, Wash.). A silicon photodiode (DET10A, Thorlabs, Newton, N.J.) was used to trigger the oscilloscope.

To analyze the signals, a MATLAB program was created which is capable of determining the penetration depth of the waveforms obtained (the code for which is set forth herein below). The MATLAB program may be obtained at http://kolbe.missouri.edu/Matlab.html, listed as PenetrationDepth.zip. In order to rapidly analyze the photoacoustic signals recorded on the oscilloscope, a graphical user interface (GUI) was developed in the MATLAB program to import the data and determine the penetration depth of a given signal. The GUI determines the penetration depth as a user-defined percentage of the maximum value of the desired photoacoustic waveform. Using the cursor, the user is able to visually define the time domain of the photoacoustic signal prior to the percent-maximum calculation in order to avoid bias due to noise and extraneous acoustic effects that might also have been recorded in the data file. The program displays the location of the percent-maximum on the plot of the original waveform in addition to displaying its value for user verification of correct penetration depth.

Chlorazol Black

Chlorazol black with an absorption coefficient of 55 cm$^{-1}$ at 532 nm was used in order to assume a low absorption condition, less than 10% absorption per interaction, to simplify the evanescent absorption equations as stated in N. Harrick, *Internal Reflection Spectroscopy*, Harrick Scientific Corporation, New York (1987). Dilutions of an initial 52.5 cm$^{-1}$ chlorazol black solution in water were also prepared. Additionally, a fluid comprising a 2% intralipid solution added to the chlorazol black were prepared, which increased the scattering of the chlorazol black to visually approximate that of β-hematin.

β-Hematin

Hemozoin is a chemical byproduct found in human blood that has been infected with malaria. However, due to the difficulty in obtaining samples of hemozoin testing with an optically analogous material was preferred for these experiments. β-hematin is a viable analogue for hemozoin in detection systems based on spectroscopic methods, such as TIRPAS, because β-hematin has the same optical and structural properties as hemozoin. β-hematin was used for testing the inventive TIRPAS system due to the availability and cost compared to actual hemozoin crystals. As a synthetically derived material, β-hematin is created by the precipitation of hematin in an acetate buffer.

The reasonably high optical absorption of β-hematin in the visible spectrum allows for the use of a standard laser harmonic wavelength, 532 nm, for photoacoustic excitation. In addition, the 100×300 nm$^2$ average size of β-hematin is on the order of the evanescent field penetration depth in the TIRPAS experiments. This should give rise to little background signal since the evanescent field cannot penetrate into larger absorbing structures such as red blood cells that are at least an order of magnitude larger than the crystals. In other words, the size of β-hematin is ideal for photoacoustic detection through TIRPAS because it is on the same order of magnitude as the penetration depth of the evanescent field, which means that the background signal from hemoglobin can be reduced by appropriately choosing the penetration depth in TIRPAS by setting the angle of excitation.

40 g of NaOH pellets were dissolved into 60 ml of stirred distilled water to create a 12.9 M NaOH solution while covering the beaker to prevent evaporation. While rapidly stirring 75 ml of 17.1 M glacial acetic acid 12.9 M NaOH was added drop-wise until the pH of the titrated buffer solution was 4.5. Distilled water was added until the total solution volume became 100 ml. 34 ml of 0.1 M NaOH solution was heated to 60° C. 175.5 mg of haemin (Sigma-Aldrich, St. Louis, Mo.) was dissolved in the NaOH solution while stirring the covered beaker. Also, 20.7 ml of the acetic acid buffer was heated to 60° C. The haemin solution was neutralized with 3.4 ml of 1M HCl solution. After stirring for five minutes, the 20.7 ml of acetic acid buffer was added to the neutralized haemin solution. The resulting solution was covered and stirred at 60° C. for 2 hours. The solution was then put in an ice bath for 10 minutes. The cooled solution was filtered over 8.0 µm nitrocellulose filter paper (Millipore, Billerica, Mass.) and the filtered precipitate was washed with distilled water and dried for 5 minutes. The solid β-hematin was desiccated for 48 hours. Finally, β-hematin was stored in PBS suspension away from light exposure at 4° C. until use.

Example 1

TIRPAS Penetration Depth, Angle Test

Figure 10A:
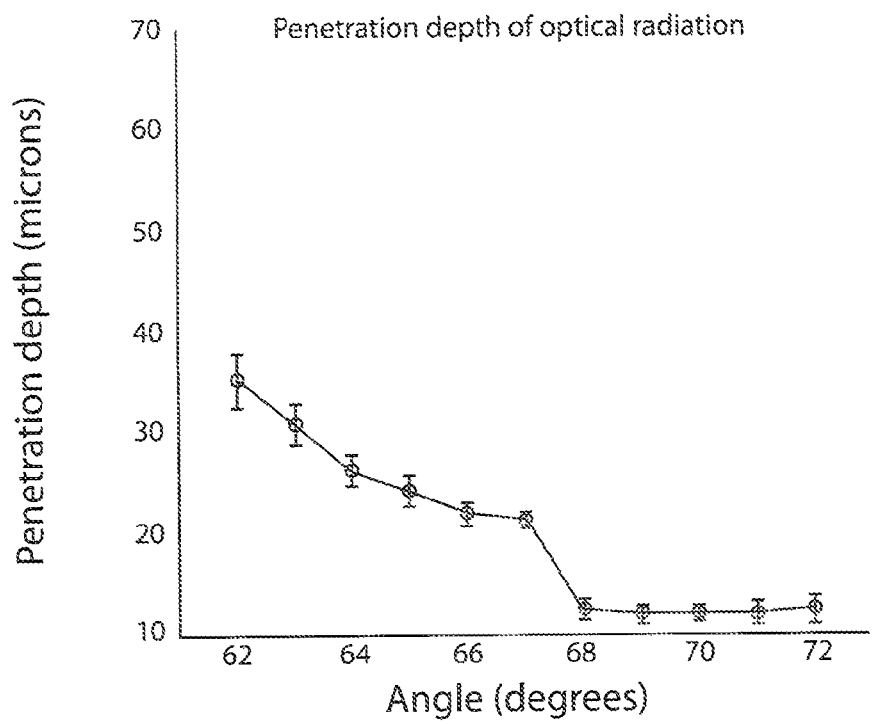
FIGS. 10A and B are graphs showing penetration depth as a function of incidence angle and the transition from photo acoustic spectroscopy (PAS) to TIRPAS.
Figure 10B:
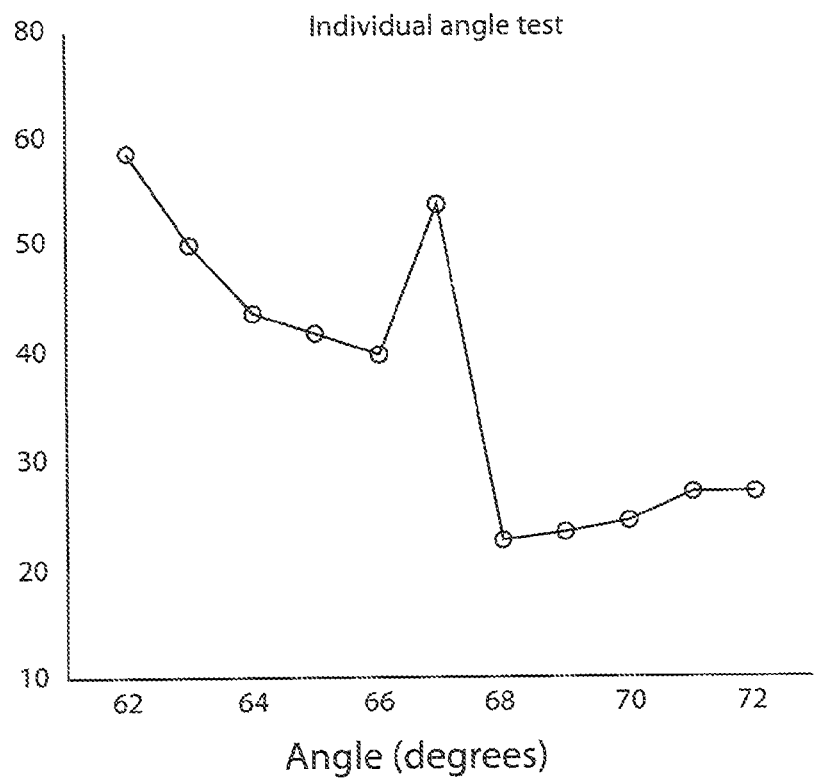

Angle testing was performed using an XYZ translational stage initially set at 72° and rotated to 62°. As the XYZ translational stage 140 moves (or rotates), the line corresponding to total internal reflection moves along the axis of the reflected beam spot. As the angle moved closer to the critical angle of about 67°, more of the spot of irradiation would become dark as the divergent part of the beam started to fall out of total internal reflection to prevent photoacoustic spectroscopy (PAS) signals from interfering with TIRPAS signals. Once the spot passes the critical angle from the total internal reflection side, the PAS side is continued to be blocked off by the spatial filter 130 until all evanescently coupled excitation was gone at a small enough angle. A sample of angles from 62° to 72° was taken to show how PAS and TIRPAS are related in a finite beam size. Since the beam size was finite, the penetration depth of the evanescent field is a function of the divergence angle from the critical angle to the edge of the beam. This experiment was performed five times and the values were averaged and are shown in FIG. 10, which shows acoustic penetration depth as determined according to the aforementioned formula for determining penetration depth ($d_p$) and may be converted to optical penetration depth as disclosed above.

Since the penetration depth of the evanescent field, even near the critical angle, is within hundreds of nanometers of the interface, most of the frequency components expected under thermal confined TIRPAS would be in the low GHz range. Since the duration of the laser pulse was 5 ns, this limited the frequency range to the maximum obtainable via a 5 ns pulse. To determine this frequency range, a simple method from J. A. Viator, *Characterization of Photoacoustic Sources in Tissue Using Time Domain Measurements*, Oregon Graduate Institute of Science & Technology, Portland, Oreg. (August 2000) was used and further assumed that a pulse duration is 5 ns f=1/$p_d$ where f is the approximate frequency maximum of the resulting wave and $p_d$ is the pulse duration of the laser.

The PVDF sensors used were reliable at frequencies up to approximately 100 MHz. Far beyond 100 MHz, the PVDF does not respond linearly to inputs. This may explain why the minimum penetration depth was sometimes twice the 7.5 µm minimum corresponding to a 5 ns pulse since the PVDF realistically stops giving consistent results beyond 10 to 15 µm penetration depth.

The maximum sampling rate of the oscilloscope used was 200 MHz which would not be enough sampling to fully capture the signals appropriately if a picosecond laser were used in order to stay within the regime of thermal confinement. However, due to the 5 nanosecond pulse duration issue mentioned above, the maximum frequency threshold was far below the maximum frequency of the oscilloscope and therefore, no distortion was expected.

Figure 11A:
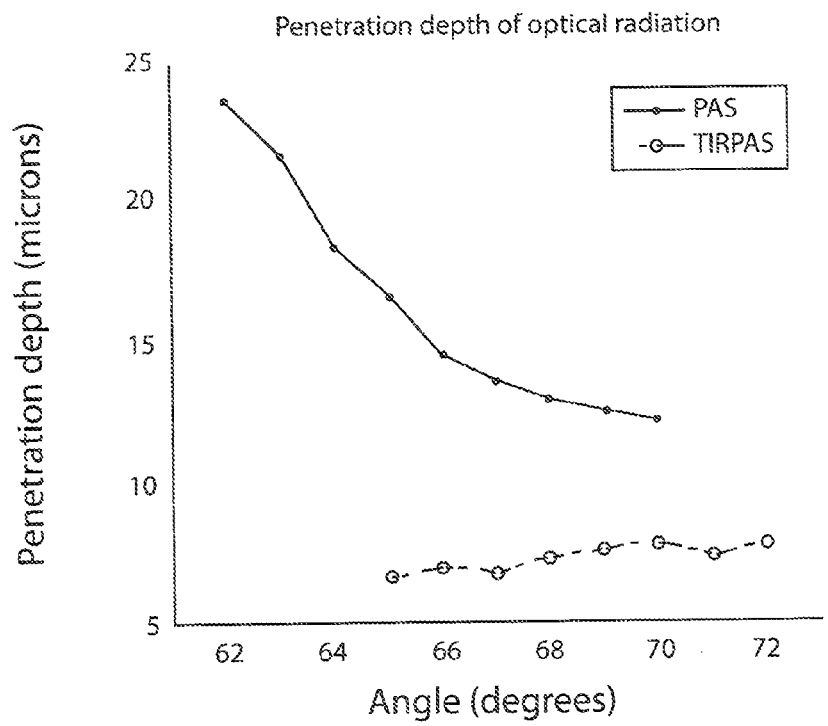
FIGS. 11A and B are graphs showing penetration depth as a function of incidence angle and photo acoustic pressure as a function of time, respectively, for PAS and TIRPAS.
Figure 11B:
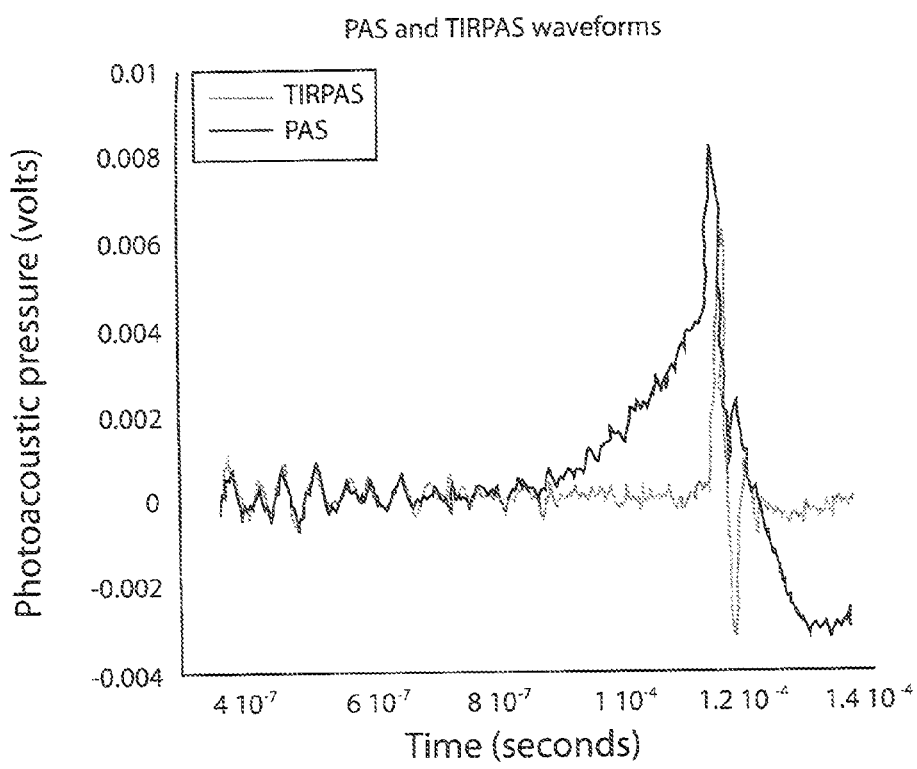

In FIG. 11, the difference in frequency components can be inferred when the penetration depths of photoacoustic spectroscopy and TIRPAS are compared. TIRPAS contains very high frequency components due to its penetration depth being on the order of a few hundred nanometers. The penetration depth of TIRPAS corresponds to a rise time of 5 ns in FIG. 11. Since the 200 MHz oscilloscope used can resolve faster differences than this, aliasing was not considered.

Figure 14A:
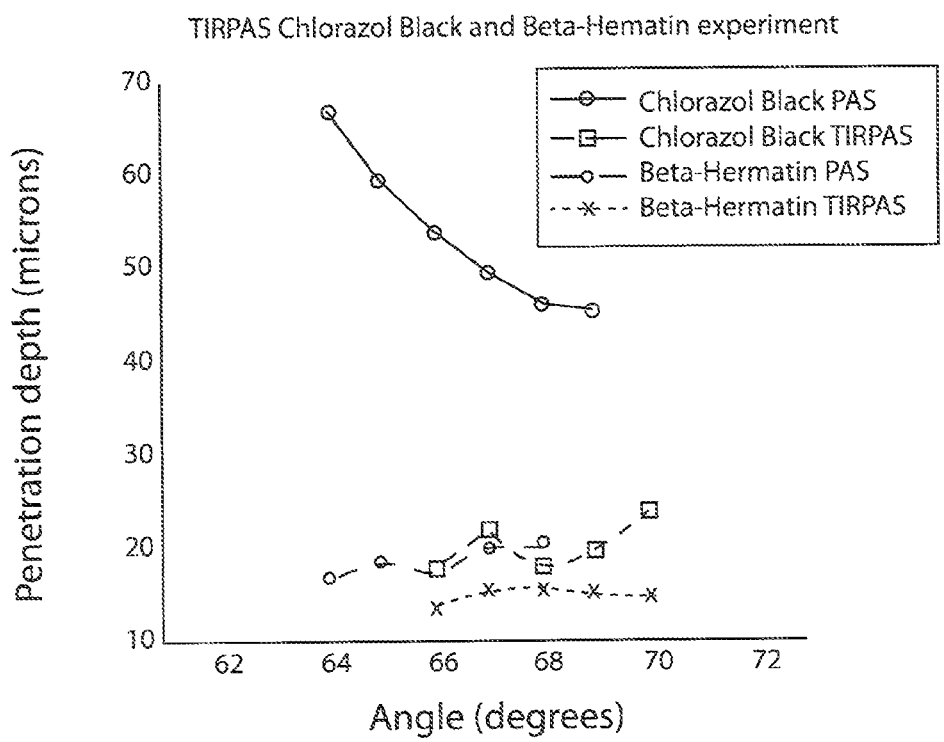
FIGS. 14A and B are graphs showing penetration depth as a function of incidence angle under PAS and TIRPAS excitation.

FIG. 14A shows the penetration depths of standard chlorazol black dye and β-hematin in both photoacoustic spectroscopy and TIRPAS excitation. The penetration depth for chlorazol black is typical for what is expected with photoacoustic spectroscopy and TIRPAS excitation. However, for β-hematin, the same setup parameters provide the same results for TIRPAS but generate different results for photoacoustic spectroscopy. From transmission electron microscopy, it is observed that the length of individual crystals is on the order of the wavelength of light used (532 nm) as well as on the order of the penetration depth, ~500 nm. Due to β-hematin's size and shape, the component for Mie scattering as well as Raleigh scattering is likely to be significant with the sample and wavelength.

Figure 14B:
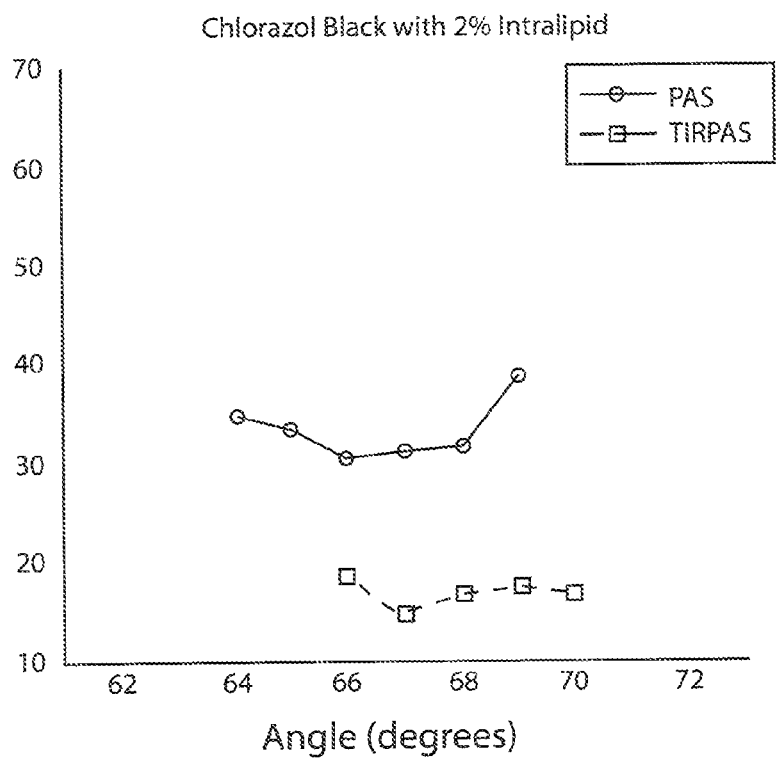

FIG. 14B right shows chlorazol black with a 2% intralipid optically scattering solution. Both TIRPAS and photoacoustic spectroscopy excitation values are much closer to each other, similar to the for β-hematin in FIG. 14A.

This effect can be explained by two factors. First, photoacoustic spectroscopy under thermal confinement displays the distribution of photons in a material. Therefore, a scatterer, by changing the distribution of photons, can change the photoacoustic effect associated with it. Also, the addition of scattering material tends to make the penetration depth smaller since the distribution of photons is affected by both $\mu_a$ and $\mu_s$.

Example 2

TIRPAS Detection Limit Test

Dilutions of chlorazol black were used to determine the approximate detection limit of the system. The laser spot was spatially filtered to produce the largest portion of the spot at the critical angle for the dilution because the penetration depth of the evanescent field is the largest under this condition.

Figure 12:
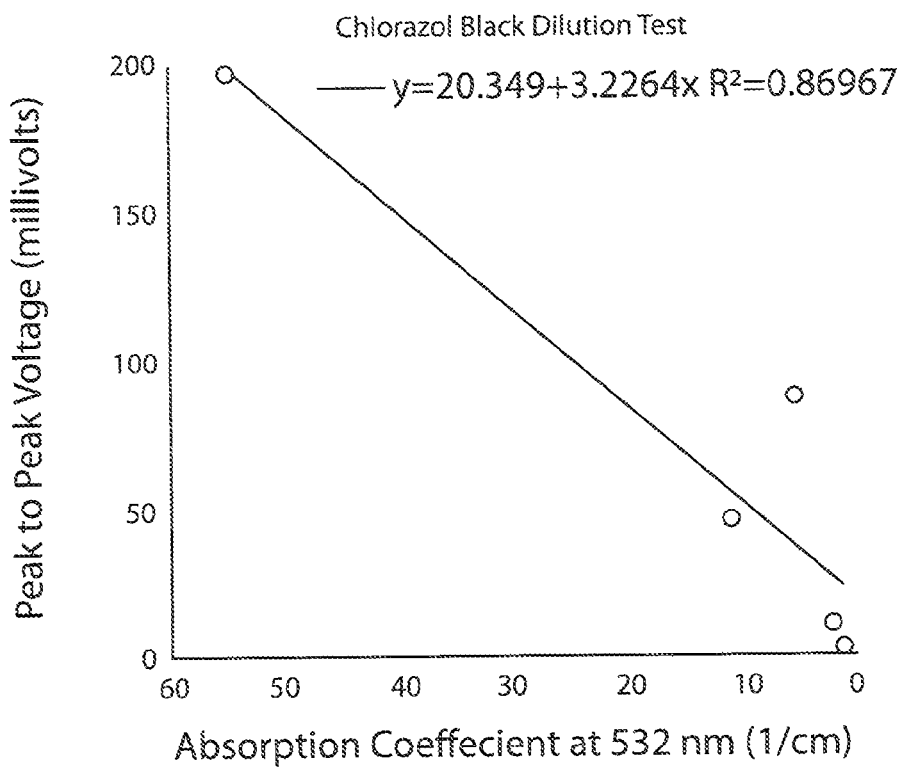
FIG. 12 is a graph of peak-to-peak voltage as a function of absorption coefficient for a chiorazol black dilution test.

FIG. 12 shows the dilution test with chlorazol black with a minimum detection limit of 1.1 cm$^{-1}$ at 2.88 millivolts peak-to-peak. The detection limit was defined by a signal to noise ratio of about 3:1. Such a low absorption would be difficult to detect using photoacoustic spectroscopy due to the very large optical path length needed for excitation.

Figure 13:
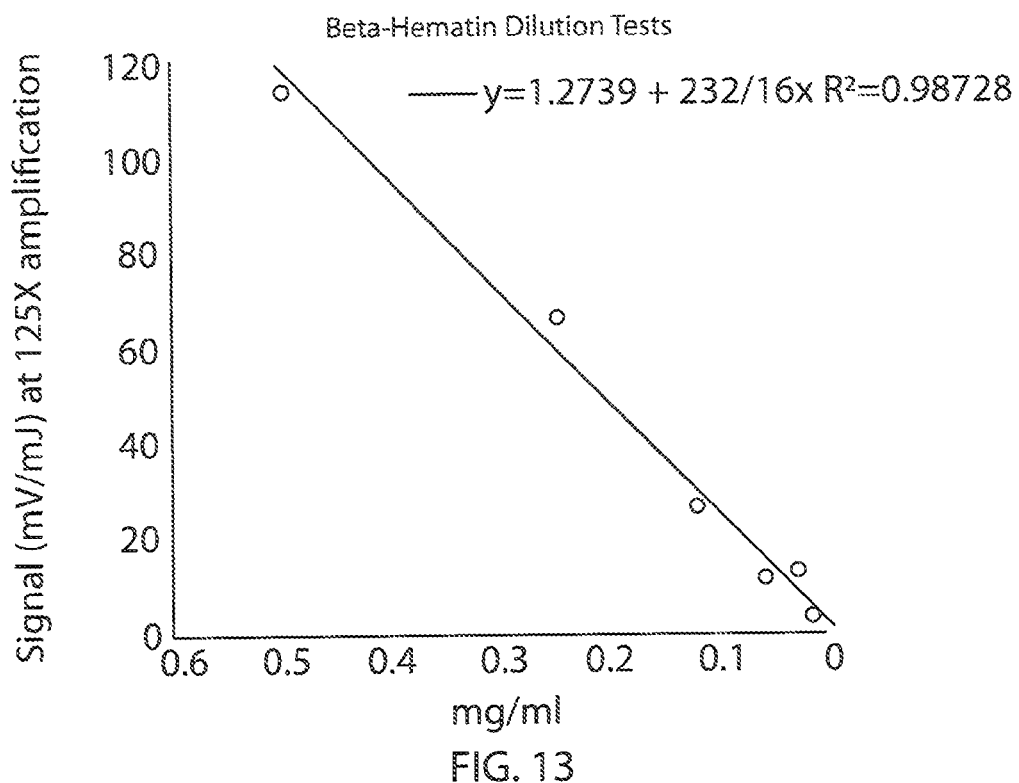
FIG. 13 is a graph of signal strength as a function of β-hematin concentration.

FIG. 13 shows the results from the dilution test on β-hematin aqueous solution under a pulsed laser beam of 532 nm at the critical angle of about 67°. As shown in FIG. 13, the detection limit of β-hematin is around 0.0156 mg/ml under the exemplary testing condition.

To compare with the conventional TIRPAS method developed by Hinoue et al., the present TIRPAS method improves the detection limit to 2.54×10$^{-5}$ absorbance units ($\mu_a$=1.1 cm$^{-1}$=2.303 cc and penetration depth is assumed to be 532 nm; A=εcL which is Beer's law to explain absorption; by substitution and assuming that L=$\delta_p$, A=($\mu_a$/2.303).

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the claims.

Penetration Depth Software Code

```
function varargout = PenetrationDepth(varargin)
%   PenetrationDepth.m - software system for plotting a individuals or groups
%                        of *.csv* files in Time and determining penetration depth
%
%       Files needed to accompany PenetrationDepth.m:
%
%           PenetrationDepth.fig - graphical user interface figure to accompany PenetrationDepth.m
%
%           loadcell.m - load *.csv* file into a matrix (embedded in oscil_csv_read)
%
%   Notes:
%       It should be noted that this software system is specifically designed for the *.csv* output from a Tektronix
%       oscilloscope and may not be compattible with all input data types (this can be easily altered by re-writing
%       oscil_csv_read to suit your needs).
%
%       It should also be noted that when any of the 'Save' buttons are pressed, the files saved are figures and as
%       such are still manipulatable within any figure window (allows for post evaluation adjustment).
%
%       Also thanks to Amos Storkey, University of Edinburgh for providing the loadcell.m function used to import
%       *.csv* files
%
%   Author: Paul Whiteside
%   E-mail: PaulWhiteside@mail.missouri.edu
%   Date: 09/24/2010; Version: 1.0
%
%   PENETRATIONDEPTH M-file for PenetrationDepth.fig
%       PENETRATIONDEPTH, by itself, creates a new PENETRATIONDEPTH or raises the existing
%       singleton*.
%
%       H = PENETRATIONDEPTH returns the handle to a new PENETRATIONDEPTH or the handle to the
%       existing singleton*.
%
%       PENETRATIONDEPTH('CALLBACK',hObject,eventData,handles,...) calls the local function named
%       CALLBACK in PENETRATIONDEPTH.M with the given input arguments.
%
%       PENETRATIONDEPTH('Property','Value',...) creates a new PENETRATIONDEPTH or raises the existing
```

```
%       singleton*. Starting from the left, property value pairs are applied to the GUI before
%       PenetrationDepth_OpeningFcn gets called. An unrecognized property name or invalid value makes
%       Property application stop. All inputs are passed to PenetrationDepth_OpeningFcn via varargin.
%
%       *See GUI Options on GUIDE's Tools menu. Choose "GUI allows only one instance to run (singleton)".
%
% See also: GUIDE, GUIDATA, GUIHANDLES
% Edit the above text to modify the response to help PenetrationDepth
% Last Modified by GUIDE v2.5 24-Sep-2010 15:06:01
% Begin initialization code - DO NOT EDIT
gui_Singleton = 1;
gui_State = struct('gui_Name',      mfilename, ...
           'gui_Singleton', gui_Singleton, ...
           'gui_OpeningFcn', @PenetrationDepth_OpeningFcn, ...
           'gui_OutputFcn', @PenetrationDepth_OutputFcn, ...
           'gui_LayoutFcn', [] , ...
           'gui_Callback',  []);
if nargin && ischar(varargin{1})
    gui_State.gui_Callback = str2func(varargin{1});
end if nargout
    [varargout{1:nargout}] = gui_mainfcn(gui_State, varargin{:});
else
    gui_mainfcn(gui_State, varargin{:});
end
% End initialization code - DO NOT EDIT % --- Executes just before PenetrationDepth is made visible.
function PenetrationDepth_OpeningFcn(hObject, eventdata, handles, varargin)
% This function has no output args, see OutputFcn.
% hObject    handle to figure
% eventdata  reserved - to be defined in a future version of MATLAB
% handles    structure with handles and user data (see GUIDATA)
% varargin   command line arguments to PenetrationDepth (see VARARGIN)

% Choose default command line output for PenetrationDepth
```

```
handles.output = hObject;

% ----- Custom Start Up Code ------------------------------------- movegui(hObject,'center')

clc

% set the initial directory to the current Matlab directory
handles.CSVfolder = cd;

set(handles.txtFolder,'string',handles.CSVfolder);
handles = LoadCSVlist(handles);

% Update handles structure
guidata(hObject, handles);

% ---- End Start Up Code ----------------------------------------

% Load CSV list
% function to load all of the *.csv* files in the chosen directory to the list box: handles.lstCSVlist function handles = LoadCSVlist(handles)

global ListOfCSVnames
clear global ListOfCSVnames
ListOfCSVnames = {};
folder = handles.CSVfolder;

% Provide for potential errors - folder does not exist, no folder specified
if ~isempty(handles.CSVfolder)
    if exist(folder,'dir') == false
        msgboxes(['Folder' folder ' does not exist'])
        return
    end
else
    msgboxes('No folder specified as input for function: LoadCSVlist.')
```

```
        return
end

CSVfiles = dir([handles.CSVfolder '/*.*']);

%   Display only *.csv* files in the folder to ease cluttering issues
for zz = 1:length(CSVfiles)
    baseFileName = CSVfiles(zz).name;
    [folder,name,extension,version] = fileparts(baseFileName);
    extension = upper(extension);

switch lower(extension)
        case('.csv')
            ListOfCSVnames = [ListOfCSVnames baseFileName];
        otherwise
    end
end set(handles.lstCSVlist,'string',ListOfCSVnames);
return %   CSVread %   function to read CSV files using the loadcell.m program and output X and Y matrices function [X,Y] = CSVread(fullCSVfileName)

[a,b,c] = loadcell(fullCSVfileName,[',' char(9)],'"','empty2num');

x_1 = a(1:3,3);
x_2 = a(4:6,1);
x_3 = a(7:18,3);
x_4 = a(19:2500,1);

X_cell = [x_1;x_2;x_3;x_4];

X = cell2mat(X_cell);
```

```
y_1 = a(1:3,4);
y_2 = a(4:6,2);
y_3 = a(7:18,4);
y_4 = a(19:2500,2);

Y_cell = [y_1;y_2;y_3;y_4];

Y = cell2mat(Y_cell);

return

% UIWAIT makes PenetrationDepth wait for user response (see UIRESUME)
% uiwait(handles.figure1);

% --- Outputs from this function are returned to the command line.
function varargout = PenetrationDepth_OutputFcn(hObject, eventdata, handles)
% varargout    cell array for returning output args (see VARARGOUT);
% hObject      handle to figure
% eventdata    reserved - to be defined in a future version of MATLAB
% handles      structure with handles and user data (see GUIDATA)

% Get default command line output from handles structure
varargout{1} = handles.output;

% CSV List Selection

% --- Executes on selection change in lstCSVlist.
function lstCSVlist_Callback(hObject, eventdata, handles)
% hObject      handle to lstCSVlist (see GCBO)
% eventdata    reserved - to be defined in a future version of MATLAB
% handles      structure with handles and user data (see GUIDATA)

% Hints: contents = get(hObject,'String') returns lstCSVlist contents as cell array
%        contents{get(hObject,'Value')} returns selected item from lstCSVlist clear global X
```

```
clear global fullCSVfileName
global baseCSVfileName
cla(handles.axesTime,'reset')

set(gcf,'Pointer','watch');
drawnow;

%   Limit selection to one file at a time
Selected = get(handles.lstCSVlist,'value');

if length(Selected) > 1
    baseCSVfileName = '';
    set(handles.btnPlotFile,'enable','off');
    set(gcf,'Pointer','arrow');
    drawnow;
    return
end set(handles.axesTime,'visible','off');

%   obtain file name and location
global fullCSVfileName

ListOfCSVnames = get(handles.lstCSVlist,'string');
baseCSVfileName = strcat(cell2mat(ListOfCSVnames(Selected)));
fullCSVfileName = [handles.CSVfolder '/' baseCSVfileName];

[folder,baseFileName,extension,version] = fileparts(fullCSVfileName);

%   provided the file is a *.csv*, plot the time domains
switch lower(extension)
    case '.csv'
        global X
        global Y
        [X,Y] = CSVread(fullCSVfileName);

plot(handles.axesTime,X,Y);
```

```
    xlabel(handles.axesTime,'time (s)');
    axis(handles.axesTime,[min(X) max(X) (min(Y)-0.2*abs(min(Y))) (max(Y)+0.2*max(Y))]);

title_string = ['Time - ' baseFileName];
    title(handles.axesTime,title_string);

set(gcf,'Pointer','arrow');
    return
  otherwise
end guidata(hObject, handles);

% --- Executes during object creation, after setting all properties.
function lstCSVlist_CreateFcn(hObject, eventdata, handles)
% hObject    handle to lstCSVlist (see GCBO)
% eventdata  reserved - to be defined in a future version of MATLAB
% handles    empty - handles not created until after all CreateFcns called % Hint: listbox controls usually have a white background on Windows.
%       See ISPC and COMPUTER.
if ispc && isequal(get(hObject,'BackgroundColor'), get(0,'defaultUicontrolBackgroundColor'))
    set(hObject,'BackgroundColor','white');
end %  Save Time Figure Button % --- Executes on button press in btnSave.
function btnSave_Callback(hObject, eventdata, handles)
% hObject    handle to btnSave (see GCBO)
% eventdata  reserved - to be defined in a future version of MATLAB
% handles    structure with handles and user data (see GUIDATA)

global fullCSVfileName

FigFileName = [fullCSVfileName(1:length(fullCSVfileName)-4) ' - Time'];
```

```
newFig = figure;
newAxes = copyobj(handles.axesTime,newFig);
set(newAxes,'Units','default','Position','default')

saveas(newFig,FigFileName,'fig')
close(newFig)

set(hObject,'String','Figure Saved...')
pause(1)
set(hObject,'String','Save Time Domain')

guidata(hObject,handles);

%   Select Folder Button

%   --- Executes on button press in btnSelectFolder.
function btnSelectFolder_Callback(hObject, eventdata, handles)
%   hObject     handle to btnSelectFolder (see GCBO)
%   eventdata   reserved - to be defined in a future version of MATLAB
%   handles     structure with handles and user data (see GUIDATA)

%   ui directory selection window
directoryValue = uigetdir(handles.CSVfolder, 'Select Folder');

if directoryValue ~= 0
    handles.CSVfolder = directoryValue;
    LoadCSVlist(handles);
    set(handles.txtFolder,'String',handles.CSVfolder)
    guidata(hObject,handles);
end guidata(hObject, handles);

function txteditPercentMax_Callback(hObject, eventdata, handles)
%   hObject     handle to txteditPercentMax (see GCBO)
%   eventdata   reserved - to be defined in a future version of MATLAB
```

% handles    structure with handles and user data (see GUIDATA)

% Hints: get(hObject,'String') returns contents of txteditPercentMax as text
%        str2double(get(hObject,'String')) returns contents of txteditPercentMax as a double % --- Executes during object creation, after setting all properties.
function txteditPercentMax_CreateFcn(hObject, eventdata, handles)
% hObject    handle to txteditPercentMax (see GCBO)
% eventdata  reserved - to be defined in a future version of MATLAB
% handles    empty - handles not created until after all CreateFcns called % Hint: edit controls usually have a white background on Windows.
%       See ISPC and COMPUTER.
if ispc && isequal(get(hObject,'BackgroundColor'),
get(0,'defaultUicontrolBackgroundColor'))
    set(hObject,'BackgroundColor','white');
end % Calculate Percent Maximum % --- Executes on button press in btnCalculate.
function btnCalculate_Callback(hObject, eventdata, handles)
% hObject    handle to btnCalculate (see GCBO)
% eventdata  reserved - to be defined in a future version of MATLAB
% handles    structure with handles and user data (see GUIDATA)

clc hold(handles.axesTime)
global X
global Y
global baseCSVfileName
global percentMax
global percentTime
clear X_coord
clear Y_coord

```
X_coord = zeros(1,2);
Y_coord = zeros(1,2);

for zz = 1:2
    [X_coord(zz),Y_coord(zz)] = ginput(1);
end cla(handles.axesTime)

plot(handles.axesTime,X,Y);
xlabel(handles.axesTime,'time (s)');

title_string = ['Time - ' baseCSVfileName];
title(handles.axesTime,title_string);
axis(handles.axesTime,[min(X) max(X) (min(Y)-0.2*abs(min(Y))) (max(Y)+0.2*max(Y))]);

plot(handles.axesTime,[X_coord(1) X_coord(1)],[-0.01 0.01],'r')
plot(handles.axesTime,[X_coord(2) X_coord(2)],[-0.01 0.01],'r')

set(gcf,'Pointer','watch');
drawnow;

X_new = [];
Y_new = [];
for ii = 1:length(X)
    if X(ii) >X_coord(1) && X(ii) < X_coord(2)
        X_new = [X_new X(ii)];
        Y_new = [Y_new Y(ii)];

maxY = max(Y_new);
    end
end for jj = 1:length(X)
    if X(jj) > X_coord(1) && X(jj) < X_coord(2)
        if Y(jj) == maxY
            maxY = Y(jj);
```

```
        maxPosition = jj;
        maxTime = X(jj);
        break
      end
    end
end maxValueString = ['Max Height: ' num2str(maxY)];
set(handles.txtMaxHeight,'String',maxValueString);
maxTimeString = ['Time at Max: ' num2str(maxTime)];
set(handles.txtMaxTime,'String',maxTimeString);

[minY,minPosition] = min(Y);
minTime = X(minPosition);
minValueString = ['Min Height: ' num2str(minY)];
set(handles.txtMinHeight,'String',minValueString);
minTimeString = ['Time at Min: ' num2str(minTime)];
set(handles.txtMinTime,'String',minTimeString);

PeakToPeakString = ['Peak to Peak: ' num2str(abs(maxY)+abs(minY))];
set(handles.txtPeakToPeak,'String',PeakToPeakString);

percentMax = .01*str2double(get(handles.txteditPercentMax,'String'))*maxY;

for kk = 1:maxPosition
    if Y(kk) < percentMax
       PercentPosition = kk;
    end
end percentTime = X(PercentPosition);

percentMaxString = ['%Max Height: ' num2str(percentMax)];
set(handles.txtPercentMax,'String',percentMaxString);
percentTimeString = ['Time at %Max: ' num2str(percentTime)];
set(handles.txtPercentTime,'String',percentTimeString);
```

```
deltaT = abs(maxTime - percentTime);

set(handles.txtDeltaT,'String',['D T: ' num2str(deltaT)]);

set(gcf,'Pointer','arrow');
drawnow hold(handles.axesTime)
%   update handle graphics
guidata(hObject, handles);

% --- Executes on button press in btnPlotPosition.
function btnPlotPosition_Callback(hObject, eventdata, handles)
% hObject    handle to btnPlotPosition (see GCBO)
% eventdata  reserved - to be defined in a future version of MATLAB
% handles    structure with handles and user data (see GUIDATA)

global percentMax
global percentTime
global X
global Y
global baseCSVfileName clc plot(handles.axesTime,X,Y,percentTime,percentMax,'r*');
xlabel(handles.axesTime,'time (s)');

title_string = ['Time - ' baseCSVfileName];
title(handles.axesTime,title_string);
axis(handles.axesTime,[min(X) max(X) (min(Y)-0.2*abs(min(Y))) (max(Y)+0.2*max(Y))]);

%   update handle graphics
guidata(hObject,handles)

%   Help Button
```

```
%   --- Executes on button press in btnHelp.
function btnHelp_Callback(hObject, eventdata, handles)
%   hObject     handle to btnHelp (see GCBO)
%   eventdata   reserved - to be defined in a future version of MATLAB
%   handles     structure with handles and user data (see GUIDATA)

InstructionsCell = {'Instructions:';'   (0) Dont Panic';...
    '   (1) Click "Select Folder" to choose a directory';...
    '   (2) Select a file from the list';...
    '   (3) Input the desired value for the percent maximum calculation';...
    '   (4) Click "Calculate" to begin the calculation';...
    '       (a) Using the cursors, define the domain that contains the';...
    '           local maximum';...
    '   (5) Click "Plot Position" to re-plot the graph with the percent max';...
    '   (6) Click "Save Figure" to save the graph as a .fig in the';...
    '       same directory';''};

msgbox(InstructionsCell,'Instructions','help')
```

What is claimed is:

1. A system for conducting total internal reflection photoacoustic spectroscopy (TIRPAS), the system comprising:
   a pulsed laser source for emitting a thermally or stress confined laser beam;
   a prism comprising a surface to be in contact with a sample that is to be subjected to TIRPAS, wherein the laser beam and the prism, when conducting TIRPAS, are configured such that the laser beam travels through the prism to a location at an interface between the prism and the sample at an angle of incidence such that an evanescent field extending into the sample forms; and
   a detector for determining whether a photoacoustic response to the evanescent field is generated by an analyte in the sample.

2. The system of claim 1, wherein the beam is thermally confined and the pulsed laser source is a Q-switched Nd:YAG laser, the prism is a right-angle prism, and the detector is a transducer.

3. The system of claim 2, wherein the transducer is a piezoelectric copolymer.

4. The system of claim 1 further comprising an XYZ translational stage and an electric motor to affect movement of the XYZ translational stage to which the prism is to be mounted when conducting TIRPAS to facilitate adjustment of the location at the interface to which the beam travels, the angle of incidence, or both.

5. The system of claim 1 further comprising one or more of the following:
   a collimator for enhancing the collimation of the laser beam before the laser beam enters the prism;
   a spatial filter for filtering the portions of the laser beam;
   a variable aperture for reducing diffraction in the laser beam;
   a beam expander for expanding the laser beam; and
   a beam splitter for enhancing the collimation of the laser beam before the laser beam enters the prism.

6. The system of claim 1 further comprising an amplifier for amplifying the detected photoacoustic response to the evanescent field generated by the analyte in the sample.

7. The system of claim 6, wherein the amplifier is selected from the group consisting of a broadband amplifier.

8. The system of claim 1 further comprising a processor configured to detect the photoacoustic response to the evanescent field generated by the analyte.

9. The system of claim 8, wherein the processor is further configured to analyze the photoacoustic response to the evanescent field generated by the analyte.

10. A method of conducting total internal reflection photoacoustic spectroscopy (TIRPAS), the method comprising:
    directing a thermally or stress confined laser beam at a prism comprising a surface in contact with a sample at an angle of incidence, wherein the laser beam and the prism are configured such that the laser beam travels through the prism to a location at an interface between the prism and the sample and forms an evanescent field extending into the sample; and
    determining whether a photoacoustic response to the evanescent field is generated by an analyte in the sample.

11. The method of claim 10, wherein the laser beam is thermally confined and the pulse laser source is a Q-switched Nd:YAG laser, the prism is a right-angle prism, and the detector is a transducer.

12. The method of claim 11, wherein the transducer is a piezoelectric copolymer.

13. The method of claim 10 further comprising adjusting the angle of incidence of the laser beam, the location at the interface to which the laser beam travels, or both when conducting TIRPAS.

14. The method of claim 13, wherein the adjusting step is performed by an XYZ translational stage to which the prism is mounted and an electric motor to affect movement of the XYZ translational stage.

15. The method of claim 10 further comprising one or more of the following:
    collimating the laser beam before the laser beam enters the prism;
    filtering a portion of the laser beam with a spatial filter;
    reducing diffraction in the laser beam with a variable aperture; and
    expanding the laser beam by using a beam expander.

16. The method of claim 10 further comprising amplifying the detected photoacoustic response to the evanescent field generated by the analyte in the sample by using an amplifier.

17. The method of claim 16, wherein the amplifier is a broadband amplifier.

18. The method of claim 10, wherein the detecting step is performed by a processor.

19. The method of claim 18, further comprising analyzing the detected photoacoustic response to the evanescent field generated by the analyte with the processor.

* * * * *